US012774299B2

(12) United States Patent
Amano et al.

(10) Patent No.: US 12,774,299 B2
(45) Date of Patent: Oct. 27, 2026

(54) SHORT-CHAIN CpG-CONTAINING OLIGODEOXYNUCLEOTIDE WITH LINKED POLYDEOXYADENYLIC ACID, COMPLEX CONTAINING SAID OLIGODEOXYNUCLEOTIDE, AND USE THEREOF

(71) Applicant: NAPAJEN PHARMA, INC.

(72) Inventors: Kanako Amano, Koganei (JP); Atsushi Uno, Koganei (JP)

(73) Assignee: NapaJen Pharma, Inc., Seattle, WA (US)

( * ) Notice: Subject to any disclaimer, the term of this patent is extended or adjusted under 35 U.S.C. 154(b) by 1097 days.

(21) Appl. No.: 17/758,036

(22) PCT Filed: Dec. 24, 2020

(86) PCT No.: PCT/JP2020/048605

§ 371 (c)(1),
(2) Date: Jun. 27, 2022

(87) PCT Pub. No.: WO2021/132528

PCT Pub. Date: Jul. 1, 2021

(65) Prior Publication Data

US 2023/0053708 A1 Feb. 23, 2023

(30) Foreign Application Priority Data

Dec. 25, 2019 (JP) ................................ 2019-235078

(51) Int. Cl.

| | |
|---|---|
| ***C12N 15/117*** | (2010.01) |
| ***A61K 31/7125*** | (2006.01) |
| ***A61K 31/716*** | (2006.01) |
| ***A61K 47/61*** | (2017.01) |
| ***A61P 37/04*** | (2006.01) |
| ***C07H 21/04*** | (2006.01) |

(52) U.S. Cl.
CPC ........... *C07H 21/04* (2013.01); *A61K 31/716* (2013.01); *A61K 47/61* (2017.08); *A61P 37/04* (2018.01); *C12N 15/117* (2013.01)

(58) Field of Classification Search
CPC .. A61K 31/716; A61K 47/61; A61K 31/7125; C12N 15/117; C12N 2310/17; C12N 2310/315; C12N 2310/3519; C12N 2320/32; C07H 21/04; A61P 37/04
See application file for complete search history.

(56) References Cited

U.S. PATENT DOCUMENTS

2003/0175731 A1 9/2003 Fearon et al.
2003/0199466 A1 10/2003 Fearon et al.
2003/0216346 A1 11/2003 Sakurai et al.
2003/0225016 A1 12/2003 Fearon et al.
2011/0189267 A1* 8/2011 Klinman ................. A61P 31/12 424/450
2015/0087027 A1 3/2015 Makarov et al.
2016/0208260 A1* 7/2016 Ishii .................... C08B 37/0024
2018/0256630 A1 9/2018 Ishii et al.

FOREIGN PATENT DOCUMENTS

EP 3 238 727 A1 11/2017
JP 2010-189400 A1 9/2010
JP 2015-510766 A1 4/2015
WO WO01/034207 A1 5/2001
WO WO 03/000922 A2 1/2003
WO WO 2015/041318 A1 3/2015
WO WO 2016/103531 A1 6/2016
WO WO 2016/152767 A1 9/2016
WO WO 2019/199945 A1 10/2019

OTHER PUBLICATIONS

International Search report issued Mar. 9, 2021 in PCT/JP2020/048605, filed on Dec. 24, 2020, citing documents AA-AF & AL-AR therein, 3 pages.
Vollmer et al. "Immunotherapeutic applications of CpG oligodeoxynucleotide TLR9 agonists", Advanced Drug Delivery Reviews, vol. 61, 2009, pp. 195-204.
Verthelyi et al. "Human Peripheral Blood Cells Differentially Recognize and Respond to Two Distinct CpG Motifs", Journal of Immunology, vol. 166, 2001, pp. 2372-2377.
Hartmann et al. "Mechanism and Function of a Newly Identified CpG DNA Motif in Human Primary B Cells", Journal of Immunology, vol. 164, 2000, pp. 944-952.
Verthelyi et al. "CpG Oligodeoxynucleotides as Vaccine Adjuvants in Primates", Journal of Immunology, vol. 168, 2014, pp. 1659-1663.

(Continued)

*Primary Examiner* — Abigail Vanhorn
(74) *Attorney, Agent, or Firm* — Oblon, McClelland, Maier & Neustadt, L.L.P.

(57) ABSTRACT

The present invention provides an oligodeoxynucleotide which comprises a CpG oligodeoxynucleotide comprising a nucleotide sequence represented by formula (1):

5'X-CpG-L-CpG-TZ3' (I)

wherein X is T or C,

L is a nucleotide sequence consisting of 1 to 7 bases, and

Z is T or C, and consisting of 8 to 16 bases, and a polydeoxyadenylic acid having a length capable of forming a complex with a β-1,3-glucan, wherein the polydeoxyadenylic acid is linked to the 3' side of the CpG oligodeoxynucleotide.

In addition, the present invention provides a complex containing said oligodeoxynucleotide and a β-1,3-glucan.

30 Claims, 10 Drawing Sheets

Specification includes a Sequence Listing.

(56) References Cited

OTHER PUBLICATIONS

Tabata et al. "Ultrasonic Degradation of Schizophyllan an Antitumor Polysaccharide Produced by *Schizophyllan commune* Fries", Carbohydrate Research, vol. 89, 1981, pp. 121-135.

Sakurai et al. "Polysaccharide-Polynucleotide Complexes.2. Complementary Polynucleotide Mimic Behavior of the natural Polysaccharide Schizophyllan in the Macromolecular Complex with Single-Stranded RNA & DNA", Biomacromolecules, vol. 2, No. 3, 2001, pp. 641-650.

Extended European Search Report issued Dec. 18, 2023, in corresponding European Patent Application No. 20905078.0, 8 pages.

K. Kobiyama et al., "Nonagonistic Dectin-1 ligand transforms CpG into a multitask nanoparticulate TLR9 agonist", Proceedings of the National Academy of Sciences, vol. 111, No. 8, Feb. 10, 2014, pp. 3086-3091.

Marshall J. D. et al., "Novel chimeric immunomodulatory compounds containing short CpG oligodeoxyribonucleotides have differential activities in human cells", Nucleic Acids Research, vol. 31, No. 17, 2003, pp. 5122-5133.

Umeharu Ohto et al., "Toll-like Receptor 9 Contains Two DNA Binding Sites that Function Cooperatively to Promote Receptor Dimerization and Activation", Immunity, vol. 48, pp. 649-658, Apr. 17, 2018.

Daijiro Tanohata et al., "Solution Properties of Nucleic Acid/β-1,3-Glucan Complexes", Kobunshi Ronbunshu, vol. 72, No. 2. pp. 37-47, Feb. 2015 (with English machine translation).

Takahisa Anada et al., "CpG DNA/zymosan complex to enhance cytokine secretion owing to the cocktail effect", Bioorganic & Medicinal Chemistry Letters, No. 16, pp. 1301-1304, 2006.

* cited by examiner

SEQUENCE LISTING

```
<160> NUMBER OF SEQ ID NOS: 99

<210> SEQ ID NO 1
<211> LENGTH: 6
<212> TYPE: DNA
<213> ORGANISM: Artificial Sequence
<220> FEATURE:
<223> OTHER INFORMATION: A3'11

<400> SEQUENCE: 1

tcgtcg                                                                  6


<210> SEQ ID NO 2
<211> LENGTH: 7
<212> TYPE: DNA
<213> ORGANISM: Artificial Sequence
<220> FEATURE:
<223> OTHER INFORMATION: A3'12

<400> SEQUENCE: 2

atcgtcg                                                                 7


<210> SEQ ID NO 3
<211> LENGTH: 8
<212> TYPE: DNA
<213> ORGANISM: Artificial Sequence
<220> FEATURE:
<223> OTHER INFORMATION: A3'13

<400> SEQUENCE: 3

gatcgtcg                                                                8


<210> SEQ ID NO 4
<211> LENGTH: 9
<212> TYPE: DNA
<213> ORGANISM: Artificial Sequence
<220> FEATURE:
<223> OTHER INFORMATION: A3'11-02

<400> SEQUENCE: 4

tcgtcgttc                                                               9
```

<210> SEQ ID NO 5
<211> LENGTH: 6
<212> TYPE: DNA
<213> ORGANISM: Artificial Sequence
<220> FEATURE:
<223> OTHER INFORMATION: gtcgtt

<400> SEQUENCE: 5 gtcgtt 6

<210> SEQ ID NO 6
<211> LENGTH: 12
<212> TYPE: DNA
<213> ORGANISM: Artificial Sequence
<220> FEATURE:
<223> OTHER INFORMATION: K23

<400> SEQUENCE: 6
tcgagcgttc tc 12

<210> SEQ ID NO 7
<211> LENGTH: 12
<212> TYPE: DNA
<213> ORGANISM: Artificial Sequence
<220> FEATURE:
<223> OTHER INFORMATION: K123

<400> SEQUENCE: 7
tcgttcgttc tc 12

<210> SEQ ID NO 8
<211> LENGTH: 10
<212> TYPE: DNA
<213> ORGANISM: Artificial Sequence
<220> FEATURE:
<223> OTHER INFORMATION: K23-01(10)

<400> SEQUENCE: 8
tcgagcgttc 10

<210> SEQ ID NO 9
<211> LENGTH: 8
<212> TYPE: DNA
<213> ORGANISM: Artificial Sequence
<220> FEATURE:
<223> OTHER INFORMATION: K23-02(8)

<400> SEQUENCE: 9 tcgagcgt 8

<210> SEQ ID NO 10
<211> LENGTH: 6
<212> TYPE: DNA
<213> ORGANISM: Artificial Sequence
<220> FEATURE:
<223> OTHER INFORMATION: K23-03(6)

<400> SEQUENCE: 10 agcgtt 6

<210> SEQ ID NO 11
<211> LENGTH: 6
<212> TYPE: DNA
<213> ORGANISM: Artificial Sequence
<220> FEATURE:
<223> OTHER INFORMATION: K23-05(6)

<400> SEQUENCE: 11 atcgac 6

<210> SEQ ID NO 12
<211> LENGTH: 9
<212> TYPE: DNA
<213> ORGANISM: Artificial Sequence
<220> FEATURE:
<223> OTHER INFORMATION: K23-06(9)

<400> SEQUENCE: 12 tcgagcgtt 9

<210> SEQ ID NO 13
<211> LENGTH: 11
<212> TYPE: DNA
<213> ORGANISM: Artificial Sequence
<220> FEATURE:
<223> OTHER INFORMATION: K23-07(11)

<400> SEQUENCE: 13
tcgagcgttc t 11

<210> SEQ ID NO 14
<211> LENGTH: 16
<212> TYPE: DNA
<213> ORGANISM: Artificial Sequence
<220> FEATURE:
<223> OTHER INFORMATION: K23-08(16)

<400> SEQUENCE: 14
actctcgagc gttctc 16

<210> SEQ ID NO 15
<211> LENGTH: 10
<212> TYPE: DNA
<213> ORGANISM: Artificial Sequence
<220> FEATURE:
<223> OTHER INFORMATION: K23-09(10)

<400> SEQUENCE: 15
tcgaacgttc 10

<210> SEQ ID NO 16
<211> LENGTH: 10
<212> TYPE: DNA
<213> ORGANISM: Artificial Sequence
<220> FEATURE:
<223> OTHER INFORMATION: K23-10(10)

<400> SEQUENCE: 16
tcggacgttc 10

<210> SEQ ID NO 17
<211> LENGTH: 10
<212> TYPE: DNA
<213> ORGANISM: Artificial Sequence
<220> FEATURE:
<223> OTHER INFORMATION: K23-11(10)

<400> SEQUENCE: 17
tcgtacgttc 10

<210> SEQ ID NO 18

<211> LENGTH: 10
<212> TYPE: DNA
<213> ORGANISM: Artificial Sequence
<220> FEATURE:
<223> OTHER INFORMATION: K23-12(10)

<400> SEQUENCE: 18
tcgatcgttc 10

<210> SEQ ID NO 19
<211> LENGTH: 9
<212> TYPE: DNA
<213> ORGANISM: Artificial Sequence
<220> FEATURE:
<223> OTHER INFORMATION: K23-13(9)

<400> SEQUENCE: 19 tcgacgttc 9

<210> SEQ ID NO 20
<211> LENGTH: 9
<212> TYPE: DNA
<213> ORGANISM: Artificial Sequence
<220> FEATURE:
<223> OTHER INFORMATION: K23-14(9)

<400> SEQUENCE: 20 tcggcgttc 9

<210> SEQ ID NO 21
<211> LENGTH: 8
<212> TYPE: DNA
<213> ORGANISM: Artificial Sequence
<220> FEATURE:
<223> OTHER INFORMATION: seq21

<400> SEQUENCE: 21 tcgacgtt 8

<210> SEQ ID NO 22
<211> LENGTH: 9
<212> TYPE: DNA
<213> ORGANISM: Artificial Sequence
<220> FEATURE:
<223> OTHER INFORMATION: seq22

<400> SEQUENCE: 22 tcgacgttt 9

<210> SEQ ID NO 23
<211> LENGTH: 9
<212> TYPE: DNA
<213> ORGANISM: Artificial Sequence
<220> FEATURE:
<223> OTHER INFORMATION: seq23

<400> SEQUENCE: 23 tctacgttc 9

<210> SEQ ID NO 24
<211> LENGTH: 8
<212> TYPE: DNA
<213> ORGANISM: Artificial Sequence
<220> FEATURE:
<223> OTHER INFORMATION: seq24

<400> SEQUENCE: 24 tctacgtt 8

<210> SEQ ID NO 25
<211> LENGTH: 9
<212> TYPE: DNA
<213> ORGANISM: Artificial Sequence
<220> FEATURE:
<223> OTHER INFORMATION: seq25

<400> SEQUENCE: 25 tcgccgtct 9

<210> SEQ ID NO 26
<211> LENGTH: 9
<212> TYPE: DNA
<213> ORGANISM: Artificial Sequence
<220> FEATURE:
<223> OTHER INFORMATION: seq26

<400> SEQUENCE: 26 tcgccgttc 9

<210> SEQ ID NO 27
<211> LENGTH: 9
<212> TYPE: DNA
<213> ORGANISM: Artificial Sequence
<220> FEATURE:
<223> OTHER INFORMATION: seq27

<400> SEQUENCE: 27 ccgacgttc 9

<210> SEQ ID NO 28
<211> LENGTH: 46
<212> TYPE: DNA
<213> ORGANISM: Artificial Sequence
<220> FEATURE:
<223> OTHER INFORMATION: A3'11-dA(s)40

<400> SEQUENCE: 28
tcgtcgaaaa aaaaaaaaaa aaaaaaaaaa aaaaaaaaaa aaaaaa 46

<210> SEQ ID NO 29
<211> LENGTH: 47
<212> TYPE: DNA
<213> ORGANISM: Artificial Sequence
<220> FEATURE:
<223> OTHER INFORMATION: A3'12-dA(s)40

<400> SEQUENCE: 29
atcgtcgaaa aaaaaaaaaa aaaaaaaaaa aaaaaaaaaa aaaaaaa 47

<210> SEQ ID NO 30
<211> LENGTH: 48
<212> TYPE: DNA
<213> ORGANISM: Artificial Sequence
<220> FEATURE:
<223> OTHER INFORMATION: A3'13-dA(s)40

<400> SEQUENCE: 30
gatcgtcgaa aaaaaaaaaa aaaaaaaaaa aaaaaaaaaa aaaaaaaa 48

<210> SEQ ID NO 31
<211> LENGTH: 49
<212> TYPE: DNA

-continued

<213> ORGANISM: Artificial Sequence
<220> FEATURE:
<223> OTHER INFORMATION: A3'11-02-dA(s)40

<400> SEQUENCE: 31
tcgtcgttca aaaaaaaaaa aaaaaaaaaa aaaaaaaaaa aaaaaaaaa 49

<210> SEQ ID NO 32
<211> LENGTH: 46
<212> TYPE: DNA
<213> ORGANISM: Artificial Sequence
<220> FEATURE:
<223> OTHER INFORMATION: gtcgtt-dA(s)40

<400> SEQUENCE: 32
gtcgttaaaa aaaaaaaaaa aaaaaaaaaa aaaaaaaaaa aaaaaa 46

<210> SEQ ID NO 33
<211> LENGTH: 52
<212> TYPE: DNA
<213> ORGANISM: Artificial Sequence
<220> FEATURE:
<223> OTHER INFORMATION: K23-dA(s)40

<400> SEQUENCE: 33
tcgagcgttc tcaaaaaaaa aaaaaaaaaa aaaaaaaaaa aaaaaaaaaa aa 52

<210> SEQ ID NO 34
<211> LENGTH: 52
<212> TYPE: DNA
<213> ORGANISM: Artificial Sequence
<220> FEATURE:
<223> OTHER INFORMATION: K123-dA(s)40

<400> SEQUENCE: 34
tcgttcgttc tcaaaaaaaa aaaaaaaaaa aaaaaaaaaa aaaaaaaaaa aa 52

<210> SEQ ID NO 35
<211> LENGTH: 50
<212> TYPE: DNA
<213> ORGANISM: Artificial Sequence
<220> FEATURE:
<223> OTHER INFORMATION: K23-01(10)-dA(s)40

<400> SEQUENCE: 35
tcgagcgttc aaaaaaaaaa aaaaaaaaaa aaaaaaaaaa aaaaaaaaaa 50

<210> SEQ ID NO 36
<211> LENGTH: 48
<212> TYPE: DNA
<213> ORGANISM: Artificial Sequence
<220> FEATURE:
<223> OTHER INFORMATION: K23-02(8)-dA(s)40

<400> SEQUENCE: 36
tcgagcgtaa aaaaaaaaaa aaaaaaaaaa aaaaaaaaaa aaaaaaaa 48

<210> SEQ ID NO 37
<211> LENGTH: 46
<212> TYPE: DNA
<213> ORGANISM: Artificial Sequence
<220> FEATURE:
<223> OTHER INFORMATION: K23-03(6)-dA(s)40

<400> SEQUENCE: 37
agcgttaaaa aaaaaaaaaa aaaaaaaaaa aaaaaaaaaa aaaaaa 46

<210> SEQ ID NO 38
<211> LENGTH: 46
<212> TYPE: DNA
<213> ORGANISM: Artificial Sequence
<220> FEATURE:
<223> OTHER INFORMATION: K23-05(6)-dA(s)40

<400> SEQUENCE: 38
atcgacaaaa aaaaaaaaaa aaaaaaaaaa aaaaaaaaaa aaaaaa 46

<210> SEQ ID NO 39
<211> LENGTH: 49
<212> TYPE: DNA
<213> ORGANISM: Artificial Sequence
<220> FEATURE:
<223> OTHER INFORMATION: K23-06(9)-dA(s)40

<400> SEQUENCE: 39
tcgagcgtta aaaaaaaaaa aaaaaaaaaa aaaaaaaaaa aaaaaaaaa 49

<210> SEQ ID NO 40
<211> LENGTH: 51
<212> TYPE: DNA
<213> ORGANISM: Artificial Sequence
<220> FEATURE:
<223> OTHER INFORMATION: K23-07(11)-dA(s)40

<400> SEQUENCE: 40
tcgagcgttc taaaaaaaaa aaaaaaaaaa aaaaaaaaaa aaaaaaaaaa a 51

<210> SEQ ID NO 41
<211> LENGTH: 56
<212> TYPE: DNA
<213> ORGANISM: Artificial Sequence
<220> FEATURE:
<223> OTHER INFORMATION: K23-08(16)-dA(s)40

<400> SEQUENCE: 41
actctcgagc gttctcaaaa aaaaaaaaaa aaaaaaaaaa aaaaaaaaaa aaaaaa 56

<210> SEQ ID NO 42
<211> LENGTH: 50
<212> TYPE: DNA
<213> ORGANISM: Artificial Sequence
<220> FEATURE:
<223> OTHER INFORMATION: K23-09(10)-dA(s)40

<400> SEQUENCE: 42
tcgaacgttc aaaaaaaaaa aaaaaaaaaa aaaaaaaaaa aaaaaaaaaa 50

<210> SEQ ID NO 43
<211> LENGTH: 50
<212> TYPE: DNA
<213> ORGANISM: Artificial Sequence
<220> FEATURE:
<223> OTHER INFORMATION: K23-10(10)-dA(s)40

<400> SEQUENCE: 43
tcggacgttc aaaaaaaaaa aaaaaaaaaa aaaaaaaaaa aaaaaaaaaa 50

<210> SEQ ID NO 44
<211> LENGTH: 50
<212> TYPE: DNA
<213> ORGANISM: Artificial Sequence
<220> FEATURE:

<223> OTHER INFORMATION: K23-11(10)-dA(s)40

<400> SEQUENCE: 44
tcgtacgttc aaaaaaaaaa aaaaaaaaaa aaaaaaaaaa aaaaaaaaaa 50

<210> SEQ ID NO 45
<211> LENGTH: 50
<212> TYPE: DNA
<213> ORGANISM: Artificial Sequence
<220> FEATURE:
<223> OTHER INFORMATION: K23-12(10)-dA(s)40

<400> SEQUENCE: 45
tcgatcgttc aaaaaaaaaa aaaaaaaaaa aaaaaaaaaa aaaaaaaaaa 50

<210> SEQ ID NO 46
<211> LENGTH: 49
<212> TYPE: DNA
<213> ORGANISM: Artificial Sequence
<220> FEATURE:
<223> OTHER INFORMATION: K23-13(9)-dA(s)40

<400> SEQUENCE: 46
tcgacgttca aaaaaaaaaa aaaaaaaaaa aaaaaaaaaa aaaaaaaaa 49

<210> SEQ ID NO 47
<211> LENGTH: 49
<212> TYPE: DNA
<213> ORGANISM: Artificial Sequence
<220> FEATURE:
<223> OTHER INFORMATION: K23-14(9)-dA(s)40

<400> SEQUENCE: 47
tcggcgttca aaaaaaaaaa aaaaaaaaaa aaaaaaaaaa aaaaaaaaa 49

<210> SEQ ID NO 48
<211> LENGTH: 48
<212> TYPE: DNA
<213> ORGANISM: Artificial Sequence
<220> FEATURE:
<223> OTHER INFORMATION: seq21-dA(s)40

<400> SEQUENCE: 48
tcgacgttaa aaaaaaaaaa aaaaaaaaaa aaaaaaaaaa aaaaaaaa 48

<210> SEQ ID NO 49
<211> LENGTH: 49
<212> TYPE: DNA
<213> ORGANISM: Artificial Sequence
<220> FEATURE:
<223> OTHER INFORMATION: seq22-dA(s)40

<400> SEQUENCE: 49
tcgacgttta aaaaaaaaaa aaaaaaaaaa aaaaaaaaaa aaaaaaaaa 49

<210> SEQ ID NO 50
<211> LENGTH: 49
<212> TYPE: DNA
<213> ORGANISM: Artificial Sequence
<220> FEATURE:
<223> OTHER INFORMATION: seq23-dA(s)40

<400> SEQUENCE: 50
tctacgttca aaaaaaaaaa aaaaaaaaaa aaaaaaaaaa aaaaaaaaa 49

<210> SEQ ID NO 51
<211> LENGTH: 48
<212> TYPE: DNA
<213> ORGANISM: Artificial Sequence
<220> FEATURE:
<223> OTHER INFORMATION: seq24-dA(s)40

<400> SEQUENCE: 51
tctacgttaa aaaaaaaaaa aaaaaaaaaa aaaaaaaaaa aaaaaaaa 48

<210> SEQ ID NO 52
<211> LENGTH: 49
<212> TYPE: DNA
<213> ORGANISM: Artificial Sequence
<220> FEATURE:
<223> OTHER INFORMATION: seq25-dA(s)40

<400> SEQUENCE: 52
tcgccgtcta aaaaaaaaaa aaaaaaaaaa aaaaaaaaaa aaaaaaaaa 49

<210> SEQ ID NO 53
<211> LENGTH: 49
<212> TYPE: DNA
<213> ORGANISM: Artificial Sequence
<220> FEATURE:
<223> OTHER INFORMATION: seq26-dA(s)40

<400> SEQUENCE: 53
tcgccgttca aaaaaaaaaa aaaaaaaaaa aaaaaaaaaa aaaaaaaaa 49

<210> SEQ ID NO 54
<211> LENGTH: 49
<212> TYPE: DNA
<213> ORGANISM: Artificial Sequence
<220> FEATURE:
<223> OTHER INFORMATION: seq27-dA(s)40

<400> SEQUENCE: 54
ccgacgttca aaaaaaaaaa aaaaaaaaaa aaaaaaaaaa aaaaaaaaa 49

<210> SEQ ID NO 55
<211> LENGTH: 9
<212> TYPE: DNA
<213> ORGANISM: Artificial Sequence
<220> FEATURE:
<223> OTHER INFORMATION: consensus seq 2

<400> SEQUENCE: 55 tcgaacgtt 9

<210> SEQ ID NO 56
<211> LENGTH: 9
<212> TYPE: DNA
<213> ORGANISM: Artificial Sequence
<220> FEATURE:
<223> OTHER INFORMATION: consensus seq 3

<400> SEQUENCE: 56 tcgatcgtt 9

<210> SEQ ID NO 57
<211> LENGTH: 9
<212> TYPE: DNA
<213> ORGANISM: Artificial Sequence
<220> FEATURE:
<223> OTHER INFORMATION: consensus seq 4

<400> SEQUENCE: 57 tcgtacgtt 9

<210> SEQ ID NO 58
<211> LENGTH: 9
<212> TYPE: DNA
<213> ORGANISM: Artificial Sequence
<220> FEATURE:
<223> OTHER INFORMATION: consensus seq 5

<400> SEQUENCE: 58 tcgttcgtt 9

<210> SEQ ID NO 59
<211> LENGTH: 9
<212> TYPE: DNA
<213> ORGANISM: Artificial Sequence
<220> FEATURE:
<223> OTHER INFORMATION: consensus seq 6

<400> SEQUENCE: 59 tcggacgtt 9

<210> SEQ ID NO 60
<211> LENGTH: 8
<212> TYPE: DNA
<213> ORGANISM: Artificial Sequence
<220> FEATURE:
<223> OTHER INFORMATION: consensus seq 8

<400> SEQUENCE: 60 tcgtcgtt 8

<210> SEQ ID NO 61
<211> LENGTH: 8
<212> TYPE: DNA
<213> ORGANISM: Artificial Sequence
<220> FEATURE:
<223> OTHER INFORMATION: consensus seq 9

<400> SEQUENCE: 61 tcggcgtt 8

<210> SEQ ID NO 62
<211> LENGTH: 8
<212> TYPE: DNA
<213> ORGANISM: Artificial Sequence
<220> FEATURE:
<223> OTHER INFORMATION: consensus seq 10

<400> SEQUENCE: 62 tcgccgtt 8

<210> SEQ ID NO 63
<211> LENGTH: 8
<212> TYPE: DNA
<213> ORGANISM: Artificial Sequence
<220> FEATURE:
<223> OTHER INFORMATION: consensus seq 11

<400> SEQUENCE: 63 ccgacgtt 8

<210> SEQ ID NO 64
<211> LENGTH: 8

<212> TYPE: DNA
<213> ORGANISM: Artificial Sequence
<220> FEATURE:
<223> OTHER INFORMATION: consensus seq 12

<400> SEQUENCE: 64 tcgccgtc 8

<210> SEQ ID NO 65
<211> LENGTH: 20
<212> TYPE: DNA
<213> ORGANISM: Artificial Sequence
<220> FEATURE:
<223> OTHER INFORMATION: K3

<400> SEQUENCE: 65
atcgactctc gagcgttctc 20

<210> SEQ ID NO 66
<211> LENGTH: 10
<212> TYPE: DNA
<213> ORGANISM: Artificial Sequence
<220> FEATURE:
<223> OTHER INFORMATION: K3-01

<400> SEQUENCE: 66
atcggcgttc 10

<210> SEQ ID NO 67
<211> LENGTH: 10
<212> TYPE: DNA
<213> ORGANISM: Artificial Sequence
<220> FEATURE:
<223> OTHER INFORMATION: K23-22

<400> SEQUENCE: 67
tcggtcgttc 10

<210> SEQ ID NO 68
<211> LENGTH: 8
<212> TYPE: DNA
<213> ORGANISM: Artificial Sequence
<220> FEATURE:
<223> OTHER INFORMATION: K23-25

<400> SEQUENCE: 68 tcgacgtc 8

<210> SEQ ID NO 69
<211> LENGTH: 9
<212> TYPE: DNA
<213> ORGANISM: Artificial Sequence
<220> FEATURE:
<223> OTHER INFORMATION: K23-26

<400> SEQUENCE: 69 tcgacgatc 9

<210> SEQ ID NO 70
<211> LENGTH: 9
<212> TYPE: DNA
<213> ORGANISM: Artificial Sequence
<220> FEATURE:
<223> OTHER INFORMATION: K23-27

<400> SEQUENCE: 70 tcgacgccc 9

<210> SEQ ID NO 71
<211> LENGTH: 11
<212> TYPE: DNA
<213> ORGANISM: Artificial Sequence
<220> FEATURE:
<223> OTHER INFORMATION: A3'13-02

<400> SEQUENCE: 71
gatcgtcgtt c 11

<210> SEQ ID NO 72
<211> LENGTH: 10
<212> TYPE: DNA
<213> ORGANISM: Artificial Sequence
<220> FEATURE:
<223> OTHER INFORMATION: A3'12-02

<400> SEQUENCE: 72
atcgtcgttc 10

<210> SEQ ID NO 73
<211> LENGTH: 15
<212> TYPE: DNA
<213> ORGANISM: Artificial Sequence
<220> FEATURE:
<223> OTHER INFORMATION: K23-28

<400> SEQUENCE: 73
tcgttttttt cgttt 15

<210> SEQ ID NO 74
<211> LENGTH: 15
<212> TYPE: DNA
<213> ORGANISM: Artificial Sequence
<220> FEATURE:
<223> OTHER INFORMATION: K23-29

<400> SEQUENCE: 74
tcgtttttta cgttc 15

<210> SEQ ID NO 75
<211> LENGTH: 15
<212> TYPE: DNA
<213> ORGANISM: Artificial Sequence
<220> FEATURE:
<223> OTHER INFORMATION: K23-30

<400> SEQUENCE: 75
tcgttcgttt cgttt 15

<210> SEQ ID NO 76
<211> LENGTH: 15
<212> TYPE: DNA
<213> ORGANISM: Artificial Sequence
<220> FEATURE:
<223> OTHER INFORMATION: K23-31

<400> SEQUENCE: 76
tcgttcgtta cgttc 15

<210> SEQ ID NO 77
<211> LENGTH: 14
<212> TYPE: DNA
<213> ORGANISM: Artificial Sequence

<220> FEATURE:
<223> OTHER INFORMATION: K23-32

<400> SEQUENCE: 77
tcgagcgagc gttc 14

<210> SEQ ID NO 78
<211> LENGTH: 44
<212> TYPE: DNA
<213> ORGANISM: Artificial Sequence
<220> FEATURE:
<223> OTHER INFORMATION: K23-14(9)-dA(s)35

<400> SEQUENCE: 78
tcggcgttca aaaaaaaaaa aaaaaaaaaa aaaaaaaaaa aaaa 44

<210> SEQ ID NO 79
<211> LENGTH: 39
<212> TYPE: DNA
<213> ORGANISM: Artificial Sequence
<220> FEATURE:
<223> OTHER INFORMATION: K23-14(9)-dA(s)30

<400> SEQUENCE: 79
tcggcgttca aaaaaaaaaa aaaaaaaaaa aaaaaaaaa 39

<210> SEQ ID NO 80
<211> LENGTH: 34
<212> TYPE: DNA
<213> ORGANISM: Artificial Sequence
<220> FEATURE:
<223> OTHER INFORMATION: K23-14(9)-dA(s)25

<400> SEQUENCE: 80
tcggcgttca aaaaaaaaaa aaaaaaaaaa aaaa 34

<210> SEQ ID NO 81
<211> LENGTH: 29
<212> TYPE: DNA
<213> ORGANISM: Artificial Sequence
<220> FEATURE:
<223> OTHER INFORMATION: K23-14(9)-dA(s)20

<400> SEQUENCE: 81
tcggcgttca aaaaaaaaaa aaaaaaaaa 29

<210> SEQ ID NO 82
<211> LENGTH: 50
<212> TYPE: DNA
<213> ORGANISM: Artificial Sequence
<220> FEATURE:
<223> OTHER INFORMATION: K3-01-dA(s)40

<400> SEQUENCE: 82
atcggcgttc aaaaaaaaaa aaaaaaaaaa aaaaaaaaaa aaaaaaaaaa 50

<210> SEQ ID NO 83
<211> LENGTH: 50
<212> TYPE: DNA
<213> ORGANISM: Artificial Sequence
<220> FEATURE:
<223> OTHER INFORMATION: K23-22-dA(s)40

<400> SEQUENCE: 83
tcggtcgttc aaaaaaaaaa aaaaaaaaaa aaaaaaaaaa aaaaaaaaaa 50

<210> SEQ ID NO 84
<211> LENGTH: 48
<212> TYPE: DNA
<213> ORGANISM: Artificial Sequence
<220> FEATURE:
<223> OTHER INFORMATION: K23-25-dA(s)40

<400> SEQUENCE: 84
tcgacgtcaa aaaaaaaaaa aaaaaaaaaa aaaaaaaaaa aaaaaaaa 48

<210> SEQ ID NO 85
<211> LENGTH: 49
<212> TYPE: DNA
<213> ORGANISM: Artificial Sequence
<220> FEATURE:
<223> OTHER INFORMATION: K23-26-dA(s)40

<400> SEQUENCE: 85
tcgacgatca aaaaaaaaaa aaaaaaaaaa aaaaaaaaaa aaaaaaaaa 49

<210> SEQ ID NO 86
<211> LENGTH: 49
<212> TYPE: DNA
<213> ORGANISM: Artificial Sequence
<220> FEATURE:
<223> OTHER INFORMATION: K23-27-dA(s)40

<400> SEQUENCE: 86
tcgacgccca aaaaaaaaaa aaaaaaaaaa aaaaaaaaaa aaaaaaaaa 49

<210> SEQ ID NO 87
<211> LENGTH: 51
<212> TYPE: DNA
<213> ORGANISM: Artificial Sequence
<220> FEATURE:
<223> OTHER INFORMATION: A3'13-02-dA(s)40

<400> SEQUENCE: 87
gatcgtcgtt caaaaaaaaa aaaaaaaaaa aaaaaaaaaa aaaaaaaaaa a 51

<210> SEQ ID NO 88
<211> LENGTH: 50
<212> TYPE: DNA
<213> ORGANISM: Artificial Sequence
<220> FEATURE:
<223> OTHER INFORMATION: A3'12-02-dA(s)40

<400> SEQUENCE: 88
atcgtcgttc aaaaaaaaaa aaaaaaaaaa aaaaaaaaaa aaaaaaaaaa 50

<210> SEQ ID NO 89
<211> LENGTH: 55
<212> TYPE: DNA
<213> ORGANISM: Artificial Sequence
<220> FEATURE:
<223> OTHER INFORMATION: K23-28-dA(s)40

<400> SEQUENCE: 89
tcgttttttt cgtttaaaaa aaaaaaaaaa aaaaaaaaaa aaaaaaaaaa aaaaa 55

<210> SEQ ID NO 90
<211> LENGTH: 55
<212> TYPE: DNA
<213> ORGANISM: Artificial Sequence
<220> FEATURE:
<223> OTHER INFORMATION: K23-29-dA(s)40

<400> SEQUENCE: 90
tcgtttttta cgttcaaaaa aaaaaaaaaa aaaaaaaaaa aaaaaaaaaa aaaaa 55

<210> SEQ ID NO 91
<211> LENGTH: 55
<212> TYPE: DNA
<213> ORGANISM: Artificial Sequence
<220> FEATURE:
<223> OTHER INFORMATION: K23-30-dA(s)40

<400> SEQUENCE: 91
tcgttcgttt cgtttaaaaa aaaaaaaaaa aaaaaaaaaa aaaaaaaaaa aaaaa 55

<210> SEQ ID NO 92
<211> LENGTH: 55
<212> TYPE: DNA
<213> ORGANISM: Artificial Sequence
<220> FEATURE:
<223> OTHER INFORMATION: K23-31-dA(s)40

<400> SEQUENCE: 92
tcgttcgtta cgttcaaaaa aaaaaaaaaa aaaaaaaaaa aaaaaaaaaa aaaaa 55

<210> SEQ ID NO 93
<211> LENGTH: 54
<212> TYPE: DNA
<213> ORGANISM: Artificial Sequence
<220> FEATURE:
<223> OTHER INFORMATION: K23-32-dA(s)40

<400> SEQUENCE: 93
tcgagcgagc gttcaaaaaa aaaaaaaaaa aaaaaaaaaa aaaaaaaaaa aaaa 54

<210> SEQ ID NO 94
<211> LENGTH: 9
<212> TYPE: DNA
<213> ORGANISM: Artificial Sequence
<220> FEATURE:
<223> OTHER INFORMATION: consensus seq 13

<400> SEQUENCE: 94 tcggtcgtt 9

<210> SEQ ID NO 95
<211> LENGTH: 14
<212> TYPE: DNA
<213> ORGANISM: Artificial Sequence
<220> FEATURE:
<223> OTHER INFORMATION: consensus seq 14

<400> SEQUENCE: 95
tcgttttttt cgtt 14

<210> SEQ ID NO 96
<211> LENGTH: 14
<212> TYPE: DNA
<213> ORGANISM: Artificial Sequence
<220> FEATURE:
<223> OTHER INFORMATION: consensus seq 15

<400> SEQUENCE: 96
tcgtttttta cgtt 14

<210> SEQ ID NO 97

-continued

```
<211> LENGTH: 14
<212> TYPE: DNA
<213> ORGANISM: Artificial Sequence
<220> FEATURE:
<223> OTHER INFORMATION: consensus seq 16

<400> SEQUENCE: 97

tcgttcgttt cgtt                                          14


<210> SEQ ID NO 98
<211> LENGTH: 14
<212> TYPE: DNA
<213> ORGANISM: Artificial Sequence
<220> FEATURE:
<223> OTHER INFORMATION: consensus seq 17

<400> SEQUENCE: 98

tcgttcgtta cgtt                                          14


<210> SEQ ID NO 99
<211> LENGTH: 13
<212> TYPE: DNA
<213> ORGANISM: Artificial Sequence
<220> FEATURE:
<223> OTHER INFORMATION: consensus seq 18

<400> SEQUENCE: 99

tcgagcgagc gtt                                           13
```

SHORT-CHAIN CpG-CONTAINING OLIGODEOXYNUCLEOTIDE WITH LINKED POLYDEOXYADENYLIC ACID, COMPLEX CONTAINING SAID OLIGODEOXYNUCLEOTIDE, AND USE THEREOF

TECHNICAL FIELD

The present invention relates to a short chain CpG-containing oligodeoxynucleotide linked with a polydeoxyadenylic acid, a complex containing said oligodeoxynucleotide, and use thereof. In detail, the present invention relates to a short chain CpG-containing oligodeoxynucleotide linked with a polydeoxyadenylic acid having an enhanced immunostimulatory activity, a complex of said oligodeoxynucleotide and a β-1,3-glucan, and medical use thereof or the like.

BACKGROUND ART

CpG oligonucleotides (CpG ODNs) are a short single strand DNA fragment containing an immunostimulatory non-methylated CG sequence (CpG motif), and are a strong agonist of Toll-like receptor9 (TLR9). The CpG ODNs activate dendritic cells (DCs) or B cells to induce production of type I interferon and inflammatory cytokines, and act as an adjuvant for Th1 type humoral and cellular immune response including cytotoxic T lymphocyte (CTL) reaction. CpG ODNs are expected to be not only an adjuvant but also an anticancer agent or antiallergic agent, since they have a strong immunostimulatory activity.

So far, four kinds of CpG ODNs (Class A, Class B, Class C, Class P) with various backbone sequences and immunostimulatory properties have been reported (Non-Patent Document 6). Of these, Class A (also called Type D) can strongly induce type I interferon production, but it is difficult to develop it clinically because it forms aggregates in a solution containing a salt due to of higher-order structure formation. On the other hand, Class B (also called Type K) contains non-palindromic and multiple CpG motifs and can strongly activate B cells to produce IL-6 without forming aggregates, but hardly induces type I interferon production (Non-Patent Documents 2 and 3). Several Class B CpG ODNs are reported in Non-Patent Document 4.

Schizophyllan (SPG) is a known soluble β-1,3-glucan derived from *Schizophyllum commune* and consists of the β-(1→3)-D-glucan main chain, and one β-(1→6)-D-glucosyl side chain per three glucoses (Non-Patent Document 5). In nature, β-1,3-glucans such as schizophyllan or the like form a triple-helix structure, but when dissolved in an alkaline solvent, the triple helix dissociates to form a single chain. When this single chain β-1,3-glucan is mixed with polydeoxyadenylic acid (dA) and neutralized, the β-1,3-glucan and poly(dA) form a complex exhibiting a triple-helix structure (Non-Patent Document 6).

Recently, it has been reported that when a poly(dA)-tail is added to the 3' end of K3, a representative Class B CpG ODN, and complexed with a β-1,3-glucan such as schizophyllan or lentinan, the complex has both an immunostimulatory activity characteristic to Class B CpG ODNs (e.g., activity to activate B cells (preferably human B cells) to produce IL-6) and an immunostimulatory activity characteristic to Class A CpG ODNs (e.g., activity to activate plasmacytoid dendritic cells to produce IFN-α), even though the complex does not contain Class A CpG ODN sequence (Patent Document 1).

CITATION LIST

Patent Documents

Patent Document 1: WO 2015/041318

Non-Patent Documents

Non-Patent Document 1: Vollmer, J. et al., Advanced drug delivery reviews 61, 195-204 (2009)
Non-Patent Document 2: Verthelyi, D. et al., Journal of immunology 166, 2372-2377 (2001)
Non-Patent Document 3: Hartmann, G. et al., Journal of immunology 164, 944-953 (2000)
Non-Patent Document 4: Verthelyi, D. et al., Journal of immunology 168, 1659-1663 (2014)
Non-Patent Document 5: Tabata, K. et al., Carbohydr. Res., 89, 121-135 (1981)
Non-Patent Document 6: Sakurai, K., et al., Biomacromolecules 2, 641-650 (2001)

SUMMARY OF THE INVENTION

Problems to be Solved by the Invention

The K3/β-1,3-glucan complex disclosed in Patent Document 1 provided a new CpG ODN that can induce type I interferon production without aggregation. However, since this complex is of an "all-in-one" type which also has IL-6 production-inducing activity, it has been desired to develop CpG ODNs with enhanced type I interferon production-inducing ability and shifted toward, rather than IL-6, type I interferon production-inducing type.

The present invention aims to provide a novel CpG ODN or a complex containing the same with enhanced type I interferon producing ability.

Means to Solve the Problems

The present inventors have investigated to further enhance the type I interferon production-inducing activity of the K3/SPG complex, and found that when a short chain CpG ODN having a specific consensus sequence, shorter than K3, was used as a CpG ODN, although the short chain CpG ODN alone had less immunostimulatory activity than K3 (Non-Patent Documents 2 and 4), the IFN-α production-inducing activity was surprisingly rather enhanced over that of K3 when the short chain CpG ODN is added with a poly(dA) tail at the 3' end and complexed with a β-1,3-glucan. The present inventors have further investigated based on these findings and completed the present invention.

Accordingly, the present invention relates to the followings.

[1] An oligodeoxynucleotide which comprises a CpG oligodeoxynucleotide comprising a nucleotide sequence represented by formula (I):

5'X-CpG-L-CpG-TZ3' (I)

wherein X is T or C,

L is a nucleotide sequence consisting of 1 to 7 bases,

Z is T or C, and consisting of 8 to 16 bases, and a polydeoxyadenylic acid having a length capable of forming a complex with a β-1,3-glucan,
wherein the polydeoxyadenylic acid is linked to the 3' side of the CpG oligodeoxynucleotide.
[2] The oligodeoxynucleotide according to [1], wherein X is T.
[3] The oligodeoxynucleotide according to [1] or [2], wherein Z is T.
[4] The oligodeoxynucleotide according to any of [1] to [3], wherein L is a nucleotide sequence represented by formula (II):

$$5'Y_1Y_2Y_3Y_4Y_5Y_6Y_7 3' \quad \text{(II)}$$

wherein $Y_1$ is a base selected from the group consisting of A, G, T and C, and
$Y_2$, $Y_3$, $Y_4$, $Y_5$, $Y_6$ and $Y_7$ are each independently not present, or are a base selected from the group consisting of A, G, T and C.
[5] The oligodeoxynucleotide according to [4], wherein $Y_3$, $Y_4$, $Y_5$, $Y_6$ and $Y_7$ are not present in formula (II).
[6] The oligodeoxynucleotide according to [5], wherein $Y_1$ is a base selected from the group consisting of A, G and T.
[7] The oligodeoxynucleotide according to [5] or [6], wherein $Y_2$ is a base selected from the group consisting of A, G and T.
[8] The oligodeoxynucleotide according to [4], wherein $Y_1$ is A or T, $Y_2$ is G or T, $Y_3$ is C or T, $Y_4$ is G or T, $Y_5$ is A or T, $Y_6$ is G or T, $Y_7$ is not present or is A or T.
[9] The oligodeoxynucleotide according to any of [1] to [8], wherein L is a nucleotide sequence selected from the group consisting of A, G, C, T, AA, AG, AT, GA, GT, TA, TT, TTTTTTT, TTTTTTA, TTCGTTT, TTCGTTA and AGCGAG.
[10] The oligodeoxynucleotide according to any of [1] to [9], wherein the CpG oligodeoxynucleotide has no additional sequence or has an additional sequence of 1 to 3 bases at the 3' side of the nucleotide sequence represented by formula (I).
[11] The oligodeoxynucleotide according to [10], wherein the additional sequence of 1 to 3 bases is a nucleotide sequence selected from the group consisting of C, CT and CTC.
[12] The oligodeoxynucleotide according to any of [1] to [11], wherein the CpG oligodeoxynucleotide has no additional sequence or has one base additional sequence at the 5' side of the nucleotide sequence represented by formula (I).
[13] The oligodeoxynucleotide according to [12], wherein the one base additional sequence is A.
[14] The oligodeoxynucleotide according to any of [1] to [13], wherein the CpG oligodeoxynucleotide consists of 8 to 15 bases.
[15] The oligodeoxynucleotide according to any of [1] to [14], wherein the CpG oligodeoxynucleotide consists of 8 to 12 bases.
[16] The oligodeoxynucleotide according to any of [1] to [15], wherein the nucleotide sequence represented by formula (I) consists of the nucleotide sequence represented by SEQ ID NO: 12, 55, 56, 57, 58, 59, 21, 60, 61, 62, 63 or 64.
[17] The oligodeoxynucleotide according to any of [1] to [15], wherein the nucleotide sequence represented by formula (I) consists of the nucleotide sequence represented by SEQ ID NO: 68, 94, 95, 96, 97, 98 or 99.
[18] The oligodeoxynucleotide according to any of [1] to [15], wherein the CpG oligodeoxynucleotide consists of the nucleotide sequence represented by SEQ ID NO: 4, 6, 7, 8, 12, 13, 14, 15, 16, 17, 18, 19, 20, 21, 22, 25, 26 or 27.
[19] The oligodeoxynucleotide according to any of [1] to [15], wherein the CpG oligodeoxynucleotide consists of the nucleotide sequence represented by SEQ ID NO: 66, 67, 68, 71, 72, 73, 74, 75, 76 or 77.
[20] The oligodeoxynucleotide according to any of [1] to [19], wherein some or all of phosphodiester bonds in the oligodeoxynucleotide are replaced by phosphorothioate bonds.
[21] The oligodeoxynucleotide according to [20], wherein all of the phosphodiester bonds in the oligodeoxynucleotide are replaced by phosphorothioate bonds.
[22] The oligodeoxynucleotide according to any of [1] to [21], wherein the length of the polydeoxyadenylic acid is 20 to 60 bases.
[23] The oligodeoxynucleotide according to any of [1] to [22], which comprises the nucleotide sequence represented by SEQ ID NO: 31, 33, 34, 35, 39, 40, 41, 42, 43, 44, 45, 46, 47, 48, 49, 52, 53 or 54.
[24] The oligodeoxynucleotide according to any of [1] to [22], which comprises the nucleotide sequence represented by SEQ ID NO: 78, 79, 80, 81, 82, 83, 84, 87, 88, 89, 90, 91,92 or 93.
[25] A complex which contains the oligodeoxynucleotide according to any of [1] to
[24] and a β-1,3-glucan.
[26] The complex according to [25], wherein the β-1,3-glucan is schizophyllan.
[27] The complex according to [25], wherein the β-1,3-glucan is curdlan.
[28] A pharmaceutical composition which contains
(i) the oligodeoxynucleotide according to any of [1] to [24], and
(ii) a β-1,3-glucan.
[29] The pharmaceutical composition according to [28], wherein the oligodeoxynucleotide of (i) forms a complex with the β-1,3-glucan of (ii).
[30] The pharmaceutical composition according to [28] or [29], wherein the 0-1,3-glucan is schizophyllan.
[31] The pharmaceutical composition according to [28] or [29], wherein the β-1,3-glucan is curdlan.
[32] The pharmaceutical composition according to any of [28] to [31], which is for immunostimulation.
[33] The pharmaceutical composition according to any of [28] to [31], which is for inducing production of type I interferon.
[34] Use of the complex according to any of [25] to [27], for the manufacture of a pharmaceutical composition for immunostimulation or for inducing production of type I interferon.
Use of the complex according to any of [25] to [27], for the manufacture of a pharmaceutical composition for inducing production of type I interferon.
[36] A method for enhancing immune response in a mammal, which comprises administering a pharmacologically effective dose of the complex according to any of [25] to [27] to the mammal.
[37] A method for inducing production of type I interferon in a mammal, which comprises administering a pharmacologically effective dose of the complex according to any of [25] to [27] to the mammal.
[38] The complex according to any of [25] to [27], for use in enhancing immune response.
[39] The complex according to any of [25] to [27], for use in inducing production of type I interferon.

[1b] An oligodeoxynucleotide which comprises a CpG oligodeoxynucleotide comprising a nucleotide sequence represented by formula (Ib):

$$5'X\text{-}CpG\text{-}Y_1Y_2\text{-}CpG\text{-}TZ3' \quad (Ib)$$

wherein

X is T or C, $Y_1$ is a base selected from the group consisting of A, G, T and C, $Y_2$ is not present, or is a base selected from the group consisting of A, G, T and C, and Z is T or C, and consisting of 8-16 bases, and a polydeoxyadenylic acid having a length capable of forming a complex with a β-1,3-glucan, wherein the polydeoxyadenylic acid is linked to the 3' side of the CpG oligodeoxynucleotide.

[2b] The oligodeoxynucleotide according to [1b], wherein X is T.

[3b] The oligodeoxynucleotide according to [1b] or [2b], wherein $Y_1$ is a base selected from the group consisting of A, G and T.

[4b] The oligodeoxynucleotide according to any of [1b] to [3b], wherein $Y_2$ is a base selected from the group consisting of A, G and T.

[5b] The oligodeoxynucleotide according to any of [1b] to [4b], wherein Z is T.

[6b] The oligodeoxynucleotide according to any of [1b] to [5b], wherein the CpG oligodeoxynucleotide has no additional sequence or has an additional sequence of 1 to 3 bases at the 3' side of the nucleotide sequence represented by formula (Ib).

[7b] The oligodeoxynucleotide according to [6b], wherein the additional sequence of 1 to 3 bases is a nucleotide sequence selected from the group consisting of C, CT and CTC.

[8b] The oligodeoxynucleotide according to any of [1b] to [7b], wherein the CpG oligodeoxynucleotide has no additional sequence at the 5' side of the nucleotide sequence represented by formula (Ib).

[9b] The oligodeoxynucleotide according to any of [1b] to [8b], wherein the CpG oligodeoxynucleotide consists of 8 to 12 bases.

[10b] The oligodeoxynucleotide according to any of [1b] to [9b], wherein the nucleotide sequence represented by formula (Ib) consists of the nucleotide sequence represented by SEQ ID NO: 12, 55, 56, 57, 58, 59, 21, 60, 61, 62, 63 or 64.

[11b] The oligodeoxynucleotide according to any of [1b] to [10b], wherein the CpG oligodeoxynucleotide consists of the nucleotide sequence represented by SEQ ID NO: 4, 6, 7, 8, 12, 13, 14, 15, 16, 17, 18, 19, 20, 21, 22, 25, 26 or 27.

[12b] The oligodeoxynucleotide according to any of [1b] to [11 b], wherein some or all of phosphodiester bonds in the oligodeoxynucleotide are replaced by phosphorothioate bonds.

[13b] The oligodeoxynucleotide according to [12b], wherein all of the phosphodiester bonds in the oligodeoxynucleotide are replaced by phosphorothioate bonds.

[14b] The oligodeoxynucleotide according to any of [1b] to [13b], wherein the length of the polydeoxyadenylic acid is 20 to 60 bases.

[15b] The oligodeoxynucleotide according to any of [1b] to [14b], which comprises the nucleotide sequence represented by SEQ ID NO: 31, 33, 34, 35, 39, 40, 41, 42, 43, 44, 45, 46, 47, 48, 49, 52, 53 or 54.

[16b] A complex which contains the oligodeoxynucleotide according to any of [1b] to [15b] and a β-1,3-glucan.

[17b] The complex according to [16b], wherein the β-1,3-glucan is schizophyllan.

[18b] A pharmaceutical composition which contains (i) the oligodeoxynucleotide according to any of [1b] to [15b], and (ii) a β-1,3-glucan.

[19b] The pharmaceutical composition according to [18b], wherein the oligodeoxynucleotide of (i) forms a complex with the β-1,3-glucan of (ii).

[20b] The pharmaceutical composition according to [18b] or [19b], wherein the β-1,3-glucan is schizophyllan.

[21b] The pharmaceutical composition according to any of [18b] to [20b], which is for immunostimulation.

[22b] The pharmaceutical composition according to any of [18b] to [20b], which is for inducing production of type I interferon.

[23b] Use of the complex according to [16b] or [17b], for the manufacture of a pharmaceutical composition for immunostimulation or for inducing production of type I interferon.

[24b] Use of the complex according to [16b] or [17b], for the manufacture of a pharmaceutical composition for inducing production of type I interferon.

[25b] A method for enhancing immune response in a mammal, which comprises administering a pharmacologically effective dose of the complex according to [16b] or [17b] to the mammal.

[26b] A method for inducing production of type I interferon in a mammal, which comprises administering a pharmacologically effective dose of the complex according to [16b] or [17b] to the mammal.

[27b] The complex according to [16b] or [17b], for use in enhancing immune response.

[28b] The complex according to [16b] or [17b], for use in inducing production of type I interferon.

Effect of the Invention

The present invention provides an oligodeoxynucleotide and a complex containing same having a strong type I interferon production-inducing activity. Since the complex of the present invention has a strong type I interferon production-inducing activity, it is useful as an immunostimulating agent for activating innate immunity or acquired immunity (especially cellular immunity) or a vaccine adjuvant.

DESCRIPTION OF EMBODIMENTS

1. Oligodeoxynucleotide

Figure 1:
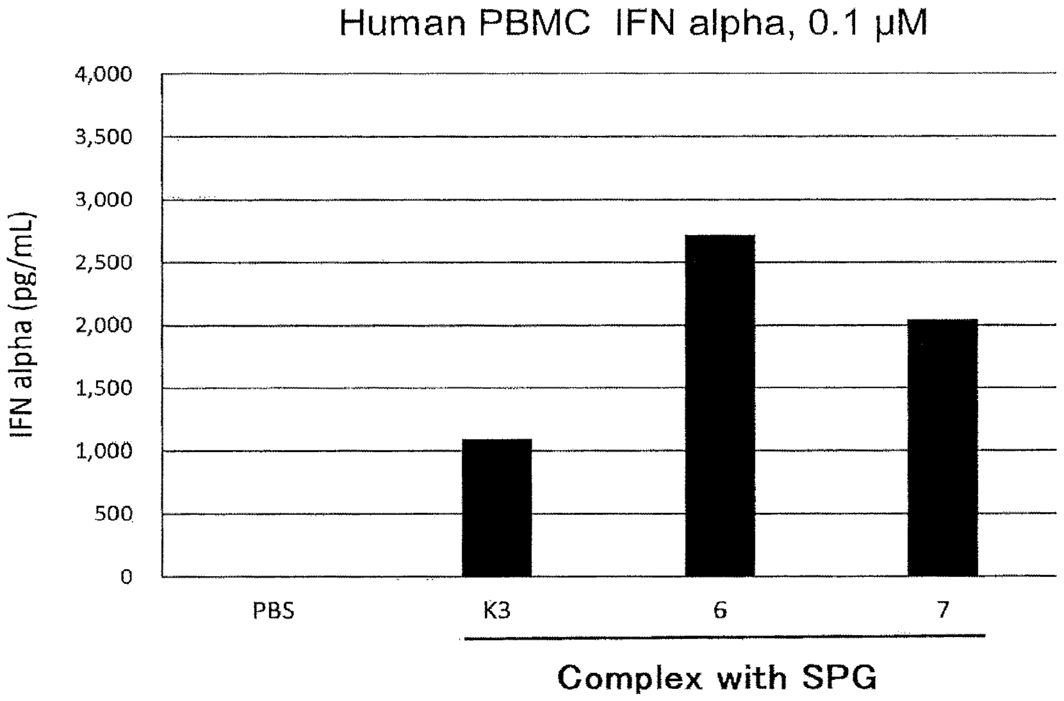
FIG. 1 shows the activity of the complex of CpG ODN-dA40 and schizophyllan to induce human PBMC IFN-α production. The numbers on the horizontal axis indicate the name of compounds.

The present invention provides an oligodeoxynucleotide which comprises a CpG oligodeoxynucleotide comprising a nucleotide sequence represented by formula (I):

5'X-CpG-L-CpG-TZ3' (I)

wherein X is T or C,

L is a nucleotide sequence consisting of 1 to 7 bases,

Z is T or C, and consisting of 8-16 bases, and a polydeoxyadenylic acid having a length capable of forming a complex with a β-1,3-glucan, wherein the polydeoxyadenylic acid is linked to the 3' side of the CpG oligodeoxynucleotide.

As used herein, the term "oligodeoxynucleotide" and the term "ODN" mean the same. In addition, the term "CpG oligodeoxynucleotide (CpG ODN)" and the term "CpG oligodeoxynucleotide (CpG ODN) residue" mean the same regardless of the presence or absence of the term "residue" at the end and are used exchangeably. The term "residue" means a partial structure of a compound having a higher molecular weight. In the present specification, those of ordinary skill in the art can easily understand from the context whether the "CpG oligodeoxynucleotide (CpG ODN)" means an independent molecule, or a partial structure of a compound having a higher molecular weight. The same applies to the terms relating to other partial structures contained in the oligodeoxynucleotide of the present invention, such as "polydeoxyadenylic acid" and the like.

CpG oligodeoxynucleotide (CpG ODN) is a single strand DNA containing an immunostimulatory unmethylated CpG motif, and is a TLR9 agonist. There are four types of CpG ODN including Class A (also called D type), Class B (also called K type), Class C and Class P, which vary in their backbone sequence and immunostimulatory property (Advanced drug delivery reviews 61, 195-204 (2009)).

Class B CpG ODN is a CpG ODN having structural and functional properties that it classically contains non-palindromic and multiple unmethylated CpG motifs, and activates B cells to produce IL-6, but scarcely induces plasmacytoid dendritic cells (pDCs) to produce IFN-α. The unmethylated CpG motif is a short nucleotide sequence containing at least one cytosine (C)-guanine (G) sequence, in which the 5-position of cytosine in the cytosine-guanine sequence is not methylated. As used herein, CpG means unmethylated CpG, unless otherwise specified.

Recently, it has been reported that when a poly(dA) tail is added to the 3' end of K3 (ategactetctegagcgttcte: SEQ ID NO: 65), a representative Class B CpG ODN, to form a complex with a β-1,3-glucan such as schizophyllan or lentinan, the complex is found to possess both the immunostimulatory activity specific to Class B CpG ODNs (e.g., activating B cells (preferably human B cells) to produce IL-6) and the immunostimulatory activity specific to Class A CpG ODNs (e.g., activating plasmacytoid dendritic cells to produce IFN-α) despite the absence of the Class A CpG ODN sequence (WO 2015/041318). The present inventors have investigated to strengthen the immunostimulatory activity of this complex further and found that when a short CpG ODN with a specific consensus sequence shorter than K3 is used as the CpG ODN and a poly(dA) tail is added to its 3' end and complexed with a β-1,3-glucan, surprisingly, the IFN-α production-inducing activity was rather enhanced as compared to the case with K3, even though the short CpG ODN alone has lower immunostimulatory activity than K3 (D. Verthelyi et al. al J. Immunol. vol. 168, no. 4, pp. 1659-1663, 2014; D. Verthelyi et al, J. Immunol. vol. 166, no. 4, pp. 2372-2377, 2001), and completed the present invention.

The CpG ODN used in the present invention comprises a nucleotide sequence represented by formula (I):

5'X-CpG-L-CpG-TZ3' (I)

wherein X is T or C,

L is a nucleotide sequence consisting of 1 to 7 bases, and

Z is T or C.

The length of the nucleotide sequence L is 1, 2, 3, 4, 5, 6 or 7 bases, and preferably 1 or 2 bases.

In one embodiment, L is a nucleotide sequence represented by formula (II):

$5'Y_1Y_2Y_3Y_4Y_5Y_6Y_73'$ (II)

wherein $Y_1$ is a base selected from the group consisting of A, G, T and C, and $Y_2$, $Y_3$, $Y_4$, $Y_5$, $Y_r$, and $Y_7$ are each independently not present, or are a base selected from the group consisting of A, G, T and C.

In said embodiment, the oligodeoxynucleotide of the present invention comprises a CpG oligodeoxynucleotide comprising a nucleotide sequence represented by formula (Ia):

$5'X\text{-CpG-}Y_1Y_2Y_3Y_4Y_5Y_6Y_7\text{-CpG-TZ}3'$ (Ia)

wherein X is T or C, $Y_1$ is a base selected from the group consisting of A, G, T and C, $Y_2$, $Y_3$, $Y_4$, $Y_5$, $Y_6$ and $Y_7$ are each independently not present, or are a base selected from the group consisting of A, G, T and C, and Z is T or C, and consisting of 8 to 16 bases, and a polydeoxyadenylic acid having a length capable of forming a complex with a 3-1,3-glucan, wherein the polydeoxyadenylic acid is linked to the 3' side of the CpG oligodeoxynucleotide.

In one embodiment, $Y_3$, $Y_4$, $Y_5$, $Y_6$ and $Y_7$ are not present in formula (II) and formula (Ia). In said embodiment, the CpG ODN used in the present invention comprises a nucleotide sequence represented by formula (Tb):

$5'X\text{-CpG-}Y_1Y_2\text{-CpG-TZ}3'$ (Ib)

wherein X is T or C, $Y_1$ is a base selected from the group consisting of A, G, T and C, $Y_2$ is not present or is a base selected from the group consisting of A, G, T and C, and Z is T or C.

In formula (Tb), $Y_1$ is preferably a base selected from the group consisting of A, G and T.

In formula (Tb), $Y_2$ is preferably a base selected from the group consisting of A, G and T.

In formula (Tb), $Y_1Y_2$ is preferably AG, AA, AT, TA, TT, GA, A, T, C or G, and more preferably AG, AA, AT, TA, TT, GA, A, T or G.

In a further aspect, $Y_1Y_2$ in formula (Tb) is preferably AG, AA, AT, TA, TT, GA, GT, A, T, C or G, and more preferably AG, AA, AT, TA, TT, GA, GT, A, T or G.

In another embodiment of formula (II) and formula (Ia), $Y_1$ is A or T, $Y_2$ is G or T, $Y_3$ is C or T, $Y_4$ is G or T, $Y_5$ is A or T, $Y_6$ is G or T, and $Y_7$ is not present or is A or T. Preferably, $Y_1Y_2Y_3Y_4Y_5Y_6Y_7$ is a nucleotide sequence selected from the group consisting of TTTTTTT, TTTTTTA, TTCGTTT, TTCGTTA and AGCGAG.

In formula (I), L is preferably a nucleotide sequence selected from the group consisting of A, G, C, T, AA, AG, AT, GA, GT, TA, TT, TTTTTTT, TTTTTTA, TTCGTTT, TTCGTTA and AGCGAG.

In formulae (I), (Ia) and (Ib), X is preferably T.

In formula (I), (Ia) and (Ib), Z is preferably T.

In one embodiment of formula (Ib),

X is T, $Y_1$ is a base selected from the group consisting of A, G and T, $Y_2$ is a base selected from the group consisting of A, G and T, and Z is T.

In one embodiment of formula (Ib),

X is T, $Y_1Y_2$ is AG, AA, AT, TA, TT, GA, GT, A, T, C or G (preferably AG, AA, AT, TA, TT, GA, UT, A, T or G), and Z is T.

In one embodiment of formula (Ib),

X is T, $Y_1Y_2$ is AG, AA, AT, TA, TT, GA, A, T, C or G (preferably AG, AA, AT, TA, TT, GA, A, T or G), and Z is T.

The nucleotide sequence represented by formula (Ib) preferably consists of a nucleotide sequence represented by SEQ ID NO: 12, 55, 56, 57, 58, 59, 21, 60, 61, 62, 63 or 64.

TABLE 1

| | |
|---|---|
| TCGAGCGTT | (SEQ ID NO: 12) |
| TCGAACGTT | (SEQ ID NO: 55) |
| TCGATCGTT | (SEQ ID NO: 56) |
| TCGTACGTT | (SEQ ID NO: 57) |
| TCGTTCGTT | (SEQ ID NO: 58) |
| TCGGACGTT | (SEQ ID NO: 59) |
| TCGACGTT | (SEQ ID NO: 21) |
| TCGTCGTT | (SEQ ID NO: 60) |
| TCGGCGTT | (SEQ ID NO: 61) |
| TCGCCGTT | (SEQ ID NO: 62) |

TABLE 1-continued

| | |
|---|---|
| CCGACGTT | (SEQ ID NO: 63) |
| TCGCCGTC | (SEQ ID NO: 64) |

In a further aspect, the nucleotide sequence represented by formula (Ib) preferably consists of a nucleotide sequence represented by SEQ ID NO: 68 or 94.

TABLE 2

| | |
|---|---|
| TCGACGTC | (SEQ ID NO: 68) |
| TCGGTCGTT | (SEQ ID NO: 94) |

In one embodiment of formula (Ia),

X is T, $Y_1$ is A or T, $Y_2$ is G or T, $Y_3$ is C or T, $Y_4$ is G or T, $Y_5$ is A or T, $Y_6$ is G or T, $Y_7$ is not present or is A or T, and Z is T.

In one embodiment of formula (Ia),

X is T, $Y_1Y_2Y_3Y_4Y_5Y_6Y_7$ is a nucleotide sequence selected from the group consisting of TTTTTTT, TTTTTTA, TTCGTTT, TTCGTTA and AGCGAG, and Z is T.

In one embodiment, the nucleotide sequence represented by formula (Ia) preferably consists of a nucleotide sequence represented by SEQ ID NO: 95, 96, 97, 98 or 99.

TABLE 3

| | |
|---|---|
| TCGTTTTTTTCGTT | (SEQ ID NO: 95) |
| TCGTTTTTTACGTT | (SEQ ID NO: 96) |
| TCGTTCGTTTCGTT | (SEQ ID NO: 97) |
| TCGTTCGTTACGTT | (SEQ ID NO: 98) |
| TCGAGCGAGCGTT | (SEQ ID NO: 99) |

The nucleotide sequence represented by formula (I) preferably consists of a nucleotide sequence represented by SEQ ID NO: 12, 55, 56, 57, 58, 59, 21, 60, 61, 62, 63, 64, 68, 94, 95, 96, 97, 98 or 99.

At the 3' side of the nucleotide sequence represented by formula (I), (Ia) or (Ib), the CpG ODN used in the present invention may or may not have an additional sequence. When it has the additional sequence, the length of the additional sequence is preferably 1 to 3 bases (i.e., 1, 2 or 3 bases). Preferably, the CpG ODN used in the present invention does not have an additional sequence, or has an additional sequence of 1 to 3 bases (i.e., 1, 2 or 3 bases) at the 3' side of the nucleotide sequence represented by formula (I), (Ta) or (Ib). When the length of the additional sequence is one base (additional sequence: $N_1$), $N_1$ is a nucleotide selected from the group consisting of A, T, C and G, preferably C or T, and more preferably C. When the length of the additional sequence is two bases (additional sequence: $N_1N_2$), $N_1$ and $N_2$ are each independently a nucleotide selected from the group consisting of A, T, C and G. $N_1$ is preferably C. $N_2$ is preferably T. The additional sequence: $N_1N_2$ is preferably CT. When the length of the additional sequence is three bases (additional sequence: $N_1N_2N_3$), $N_1$, $N_2$ and $N_3$ are each independently a nucleotide selected from the group consisting of A, T, C and G. $N_1$ is preferably C. $N_2$ is preferably T. $N_3$ is preferably C. The additional sequence: $N_1N_2N_3$ is preferably CTC. In a more preferred embodiment, the CpG ODN used in the present invention does not have an additional sequence or has an additional sequence selected from the group consisting of C, T, CT and CTC at the 3' side of the nucleotide sequence represented by formula (I), (Ia) or (Ib). In a more preferred embodiment, the CpG ODN used in the present invention does not have an additional sequence or has an additional sequence selected from the group consisting of C, CT and CTC at the 3' side of the nucleotide sequence represented by formula (I), (Ta) or (Ib).

At the 5' side of the nucleotide sequence represented by formula (I), (Ia) or (Ib), the CpG ODN used in the present invention may or may not have an additional sequence. When it has an additional sequence, the length of the additional sequence is preferably 1 to 4 bases (i.e., 1, 2, 3 or 4 bases), and more preferably one base. When the length of the additional sequence is one base, the additional sequence is a nucleotide selected from the group consisting of A, T, C and G, and preferably A. Preferably, at the 5' side of the nucleotide sequence represented by formula (I), (Ia) or (Ib), the CpG ODN used in the present invention has no additional sequence or has one base additional sequence (e.g., A), and more preferably the CpG ODN has no additional sequence at the 5' side of the nucleotide sequence represented by formula (I), (Ia) or (Ib).

In a preferred embodiment, the CpG ODN used in the present invention has no additional sequence or has an additional sequence of 1 to 3 bases (i.e., 1, 2 or 3 bases) at the 3' side of the nucleotide sequence represented by formula (I), (Ia) or (1b), and has no additional sequence at the 5' side of the nucleotide sequence represented by formula (I), (Ia) or (Ib). In a more preferred embodiment, the CpG ODN used in the present invention has no additional sequence or has an additional sequence selected from the group consisting of C, CT and CTC at the 3' side of the nucleotide sequence represented by formula (I), (Ia) or (Ib), and has no additional sequence at the 5' side of the nucleotide sequence represented by formula (I), (Ia) or (Ib).

In a further aspect, the CpG ODN used in the present invention has no additional sequence or has an additional sequence of one to three bases (i.e., 1, 2 or 3 bases) at the 3' side of the nucleotide sequence represented by formula (I), (Ia) or (Ib), and has no additional sequence or has one base additional sequence at the 5' side of the nucleotide sequence represented by formula (I), (Ia) or (Ib). More preferably, the CpG ODN used in the present invention has no additional sequence or has an additional sequence selected from the group consisting of C, CT and CTC at the 3' side of the nucleotide sequence represented by formula (I), (Ia) or (Ib), and has no additional sequence or has one base additional sequence of A at the 5' side of the nucleotide sequence represented by formula (T), (Ia) or (Ib).

The CpG ODN used in the present invention consists of 8 to 16 bases (e.g., 8, 9, 10, 11, 12, 13, 14, 15 or 16 bases), preferably 8 to 15 bases (e.g., 8, 9, 10, 11, 12, 13, 14 or 15 bases), and more preferably 8 to 12 bases (e.g., 8, 9, 10, 11 or 12 bases).

The CpG ODN used in the present invention preferably consists of a nucleotide sequence represented by SEQ ID NO: 4, 6, 7, 8, 12, 13, 14, 15, 16, 17, 18, 19, 20, 21, 22, 25, 26 or 27.

TABLE 4

| | |
|---|---|
| TCGTCGTTC | (SEQ ID NO: 4) |
| TCGAGCGTTCTC | (SEQ ID NO: 6) |
| TCGTTCGTTCTC | (SEQ ID NO: 7) |
| TCGAGCGTTC | (SEQ ID NO: 8) |
| TCGAGCGTT | (SEQ ID NO: 12) |
| TCGAGCGTTCT | (SEQ ID NO: 13) |
| ACTCTCGAGCGTTCTC | (SEQ ID NO: 14) |
| TCGAACGTTC | (SEQ ID NO: 15) |
| TCGGACGTTC | (SEQ ID NO: 16) |
| TCGTACGTTC | (SEQ ID NO: 17) |
| TCGATCGTTC | (SEQ ID NO: 18) |
| TCGACGTTC | (SEQ ID NO: 19) |
| TCGGCGTTC | (SEQ ID NO: 20) |
| TCGACGTT | (SEQ ID NO: 21) |
| TCGACGTTT | (SEQ ID NO: 22) |
| TCGCCGTCT | (SEQ ID NO: 25) |
| TCGCCGTTC | (SEQ ID NO: 26) |
| CCGACGTTC | (SEQ ID NO: 27) |

In a further aspect, the CpG ODN used in the present invention consists of a nucleotide sequence represented by SEQ ID NO: 66, 67, 68, 71, 72, 73, 74, 75, 76 or 77.

TABLE 5

| | |
|---|---|
| ATCGGCGTTC | (SEQ ID NO: 66) |
| TCGGTCGTTC | (SEQ ID NO: 67) |
| TCGACGTC | (SEQ ID NO: 68) |
| GATCGTCGTTC | (SEQ ID NO: 71) |
| ATCGTCGTTC | (SEQ ID NO: 72) |
| TCGTTTTTTTCGTTT | (SEQ ID NO: 73) |
| TCGTTTTTTACGTTC | (SEQ ID NO: 74) |
| TCGTTCGTTTCGTTT | (SEQ ID NO: 75) |
| TCGTTCGTTACGTTC | (SEQ ID NO: 76) |
| TCGAGCGAGCGTTC | (SEQ ID NO: 77) |

The length of the polydeoxyadenylic acid (dA) is not particularly limited as long as it is long enough to form a complex with a β-1,3-glucan (e.g., schizophyllan) chain. Said complex may be of a triple helix structure consisting of one polydeoxyadenylic acid (dA) chain and two β-1,3-glucan (e.g., schizophyllan) chains. From the point of view of forming a stable triple helix structure, the length of the polydeoxyadenylic acid (dA) is generally 20-nucleotide length or more, preferably 40-nucleotide length or more. Theoretically, the poly(dA) does not have the upper limit for its length, since the longer the poly(dA) is, the more stable triple helix structure is formed with a β-1,3-glucan. However, when it is too long, it may cause variations in the length of oligodeoxynucleotide during synthesis. Therefore, it is generally 80-nucleotide length or less, preferably 60-nucleotide length or less. On the other hand, from the point of view of increasing the amount of the oligodeoxynucleotide of the present invention bound per unit amount of a β-1,3-glucan, avoiding variation in length of the oligodeoxynucleotide during its synthesis, and efficiency in complex formation, as well as forming the stable triple helix structure described above, the length of the poly(dA) is preferably 20 to 60-nucleotide length (specifically, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60-nucleotide length), more preferably 30 to 50-nucleotide length (30, 31, 32, 33, 34, 35, 36, 37, 38, 39, 40, 41, 42, 43, 44, 45, 46, 47, 48, 49 or 50-nucleotide length), most preferably 30 to 45-nucleotide length (30, 31, 32, 33, 34, 35, 36, 37, 38, 39, 40, 41, 42, 43, 44 or 45-nucleotide length). In a further aspect, the length of the poly(dA) is preferably 20 to 50-nucleotide length (20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50-nucleotide length), more preferably 20 to 40-nucleotide length (specifically, 20, 21, 22, 23, 24, 25, 26, 27, 28, 29, 30, 31, 32, 33, 34, 35, 36, 37, 38, 39 or 40-nucleotide length), further preferably 25 to 40-nucleotide length (25, 26, 27, 28, 29, 30, 31, 32, 33, 34, 35, 36, 37, 38, 39 or 40-nucleotide length). Particularly, when it is 30-nucleotide length or more, good complex formation efficiency is achieved. The oligodeoxynucleotide of the present invention containing poly(dA) has an activity to form a triple-helix structure together with two β-1,3-glucan (e.g., schizophyllan) chains. Note that polydeoxyadenylic acid is sometimes indicated as "poly(dA)".

While one molecule of the oligodeoxynucleotide of the invention may contain multiple CpG ODNs and/or poly(dA)s, preferably it contains one CpG ODN and one poly(dA), most preferably it consists of one CpG ODN and one poly(dA).

The oligodeoxynucleotide of the present invention is characterized in that the poly(dA) is linked to the 3' side of the CpG ODN. The CpG ODN and the poly(dA) may be linked directly by a covalent bond or linked via a spacer sequence. The spacer sequence means a nucleotide sequence containing one or more nucleotides which is inserted between two adjacent constituent elements. While the length of the spacer sequence is not particularly limited, it is generally 1 to 10-nucleotide length, preferably 1 to 5-nucleotide length, more preferably 1 to 3-nucleotide length. Most preferably, the CpG ODN and the poly(dA) are linked together without a spacer sequence (i.e., by a covalent bond directly) to construct a single-strand oligodeoxynucleotide.

The covalent bond between the CpG ODN and the poly(dA) is a phosphodiester bond which may be appropriately modified to be resistant to the degradation in vivo (e.g., degradation by exo- or endonucleases). The modification is a phosphorothioate modification or a phosphorodithioate modification. The covalent bond between the CpG ODN and the poly(dA) is preferably a phosphorothioate-modified phosphodiester bond (i.e., a phosphorothioate bond).

The oligodeoxynucleotide of the present invention may have an additional nucleotide sequence at the 5'-end and/or the 3'-end thereof, in addition to the CpG ODN, the poly(dA) and an optional spacer sequence. While the length of the additional nucleotide sequence is not particularly limited as long as the complex of the present invention has an immunostimulatory activity (preferably an activity to activate B cells to produce IL-6, and an activity to activate dendritic cells to produce IFN-α), it is generally 1 to 10-nucleotide length, preferably 1 to 5-nucleotide length, more preferably 1 to 3-nucleotide length.

In a preferred embodiment, the oligodeoxynucleotide of the present invention does not contain an additional nucleotide sequence at the 5' end. In this embodiment, the CpG ODN is located at the most 5' end of the oligodeoxynucleotide of the present invention. In said embodiment, the oligodeoxynucleotide of the present invention consists of a CpG ODN, a poly(dA), an optional spacer sequence, and an optional additional nucleotide sequence at the 3' end, preferably consists of a CpG ODN, a poly(dA), and an optional additional nucleotide sequence at the 3' end, and more preferably consists of a CpG ODN and a poly(dA).

In a preferred embodiment, the oligodeoxynucleotide of the present invention does not contain any such additional nucleotide sequences at the 5' and 3' ends. In said embodiment, the CpG ODN is located at the most 5' end of the oligodeoxynucleotide of the present invention, and the poly (dA) is located at the most 3' end of the oligodeoxynucleotide of the present invention. In this embodiment, the oligodeoxynucleotide of the present invention preferably consists of a CpG ODN, a poly(dA) and an optional spacer sequence, and further preferably consists of a CpG ODN and a poly(dA).

In the most preferred embodiment, the oligodeoxynucleotide of the present invention consists of the above-described CpG ODN and the poly(dA), wherein the CpG ODN is located at the 5' end and the poly(dA) is located at the 3' end of the oligodeoxynucleotide, respectively.

The total length of the oligodeoxynucleotide of the present invention is generally 28 to 200-nucleotide length, preferably 30 to 100-nucleotide length, more preferably 35 to 80-nucleotide length (specifically, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleotide length), more preferably 40 to 65-nucleotide length (specifically, 40, 41, 42, 43, 44, 45, 46, 47, 48, 49, 50, 51, 52, 53, 54, 55, 56, 57, 58, 59, 60, 61, 62, 63, 64 or 65 nucleotide length), most preferably 43 to 57-nucleotide length (specifically, 43, 44, 45, 46, 47, 48, 49, 50, 51, 52, 53, 54, 55, 56 or 57-nucleotide length).

Specific examples or the oligodeoxynucleotide of the present invention include an oligodeoxynucleotide consisting of the nucleotide sequence represented by SEQ ID NO: 31, 33, 34, 35, 39, 40, 41, 42, 43, 44, 45, 46, 47, 48, 49, 52, 53 or 54.

In a further aspect, specific examples of the oligodeoxynucleotide of the present invention include an oligodeoxynucleotide consisting of the nucleotide sequence represented by SEQ ID NO: 78, 79, 80, 81, 82, 83, 84, 87, 88, 89, 90, 91, 92 or 93.

The oligodeoxynucleotide of the present invention may be appropriately modified to be resistant to the degradation in vivo (e.g., degradation by exo- or endonucleases). Preferably, the modification comprises a phosphorothioate modification or a phosphorodithioate modification. This means that some or all of phosphodiester bonds in the oligodeoxynucleotide of the present invention are replaced by phosphorothioate bonds or phosphorodithioate bonds.

Preferably, the oligodeoxynucleotide of the present invention comprises a modification of phosphodiester bond, more preferably, the modification of phosphodiester bond is a phosphorothioate bond (that is, as described in WO 95/26204, one of the non-crosslinking oxygen atoms is replaced by a sulfur atom). That is, some or all of the phosphodiester bonds in the oligodeoxynucleotide of the present invention are replaced by phosphorothioate bonds.

Preferably, the oligodeoxynucleotide of the present invention comprises a modification by a phosphorothioate bond or a phosphorodithioate bond in the CpG ODN, more preferably, all of the phosphodiester bonds in the CpG ODN are replaced by phosphorothioate bonds or phosphorodithioate bonds, and still more preferably, all of the phosphodiester bonds in the CpG ODN are replaced by phosphorothioate bonds. In addition, the oligodeoxynucleotide of the present invention preferably comprises a phosphorothioate bond or a phosphorodithioate bond in the poly(dA), more preferably, all the phosphodiester bonds in the poly(dA) are replaced by phosphorothioate bonds or phosphorodithioate bonds, and still more preferably, all the phosphodiester bonds in the poly(dA) are replaced by phosphorothioate bonds.

In a preferred embodiment, all the phosphodiester bonds contained in the oligodeoxynucleotide of the present invention are replaced by phosphorothioate bonds or phosphorodithioate bonds, and more preferably, all the phosphodiester bonds contained in the oligodeoxynucleotide of the present invention are replaced by phosphorothioate bonds.

Due to the phosphorothioate bond, enhancement of the immunostimulatory activity and high yield of the β-1,3-glucan complex as well as resistance to the degradation can be expected for the oligodeoxynucleotide of the present invention. As used herein, phosphorothioate bond and phosphodiester bond are synonymous with phosphorothioate backbone and phosphate backbone, respectively.

In one embodiment, the oligodeoxynucleotide of the present invention comprises a CpG oligodeoxynucleotide comprising a nucleotide sequence represented by formula (Ib):

$$5'X\text{-}CpG\text{-}Y_1Y_2\text{-}CpG\text{-}TZ3' \quad \text{(Ib)}$$

wherein X is T, $Y_1$ is a base selected from the group consisting of A, G and T, $Y_2$ is not present or is a base selected from the group consisting of A, G and T, and Z is T, having no additional sequence or an additional sequence of 1 to 3 bases (i.e., 1, 2 or 3 bases) at the 3' side of the nucleotide sequence represented by formula (Ib), having no additional sequence at the 5' side of the nucleotide sequence represented by formula (Ib), and consisting of 8 to 16 bases (preferably 8 to 12 bases), and a polydeoxyadenylic acid having 20 to 60-nucleotide length (preferably 30 to 50-nucleotide length, more preferably 30 to 45-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end of the polydeoxyadenylic acid, some or all of the phosphodiester bonds are replaced by phosphorothioate bonds, and the total length is 28 to 200 nucleotide-length (preferably 30 to 100-nucleotide length, more preferably 35 to 80-nucleotide length, further preferably 40 to 65-nucleotide length, still further preferably 43 to 57-nucleotide length).

In one embodiment, the oligodeoxynucleotide of the present invention comprises a CpG oligodeoxynucleotide comprising a nucleotide sequence represented by a formula (Ib):

$$5'X\text{-}CpG\text{-}Y_1Y_2\text{-}CpG\text{-}TZ3' \quad \text{(Ib)}$$

wherein X is T, $Y_1Y_2$ is AG, AA, AT, TA, TT, GA, A, T, C or G (preferably, AG, AA, AT, TA, TT, GA, A, T or G), and Z is T, having no additional sequence or an additional sequence selected from the group consisting of C, CT and CTC at the 3' side of the nucleotide sequence represented by formula (Ib), having no additional sequence at the 5' side of the nucleotide sequence represented by formula (Ib), and consisting of 8 to 16 bases (preferably 8 to 12 bases), and a polydeoxyadenylic acid having 20 to 60-nucleotide length (preferably 30 to 50-nucleotide length, more preferably 30 to 45-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end of the polydeoxyadenylic acid, some or all of the phosphodiester bonds are replaced by phosphorothioate bonds, and the total length is 28 to 200-nucleotide length (preferably 30 to 100-nucleotide length, more preferably 35 to 80-nucleotide length, further preferably 40 to 65-nucleotide length, and still further preferably 43 to 57-nucleotide length). The nucleotide sequence represented by formula (Ib) may be the nucleotide sequence represented by SEQ ID NO: 12, 55, 56, 57, 58, 59, 21, 60, 61, 62, 63 or 64.

In a further aspect, in one embodiment, the oligodeoxynucleotide of the present invention comprises a CpG oligodeoxynucleotide comprising a nucleotide sequence represented by formula (I):

$$5'X\text{-}CpG\text{-}L\text{-}CpG\text{-}TZ3' \quad \text{(I)}$$

wherein

X is T,

L is a nucleotide sequence consisting of 1 to 7 bases, and

Z is T, having no additional sequence or an additional sequence of 1 to 3 bases (i.e., 1, 2 or 3 bases) at the 3' side of the nucleotide sequence represented by formula (I), having no additional sequence or one base additional sequence at the 5' side of the nucleotide sequence represented by formula (I), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of phosphodiester bonds are replaced by phosphorothioate bonds.

The total length of the oligodeoxynucleotide may be generally 28 to 200-nucleotide length (preferably 30 to 100-nucleotide length, more preferably 35 to 80-nucleotide length, further preferably 40 to 65-nucleotide length, still further preferably 43 to 57-nucleotide length). L may be a nucleotide sequence selected from the group consisting of A, G, C, T, AA, AG, AT, GA, GT, TA, TT, TTTTTTT, TTTTTTA, TTCGTTT, TTCGTTA and AGCGAG.

In a further aspect, in one embodiment, the oligodeoxynucleotide of the present invention comprises a CpG oligodeoxynucleotide comprising a nucleotide sequence represented by a formula (Ib):

$$5'X\text{-CpG-}Y_1Y_2\text{-CpG-}TZ3' \quad \text{(Ib)}$$

wherein X is T, $Y_1$ is a base selected from the group consisting of A, G and T, $Y_2$ is not present or is a base selected from the group consisting of A, G and T, and Z is T, having no additional sequence or an additional sequence of 1 to 3 bases (i.e., 1, 2 or 3 bases) at the 3' side of the nucleotide sequence represented by formula (Ib), having no additional sequence or one base additional sequence at the 5' side of the nucleotide sequence represented by formula (Tb), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of the phosphodiester bonds are replaced by phosphorothioate bonds. The total length of the oligodeoxynucleotide may be 28 to 200-nucleotide length (preferably 30 to 100-nucleotide length, more preferably 35 to 80-nucleotide length, further preferably 40 to 65-nucleotide length, still further preferably 43 to 57-nucleotide length).

In a further aspect, in one embodiment, the oligodeoxynucleotide of the present invention comprises a CpG oligodeoxynucleotide comprising a nucleotide sequence represented by formula (Ib):

$$5'X\text{-CpG-}Y_1Y_2\text{-CpG-}TZ3' \quad \text{(Ib)}$$

wherein X is T, $Y_1Y_2$ is AG, AA, AT, TA, TT, GA, GT, A, T, C or G (preferably, AG, AA, AT, TA, TT, GA, GT, A, T or G), and Z is T, having no additional sequence or an additional sequence selected from the group consisting of C, T, CT and CTC at the 3' side of the nucleotide sequence represented by formula (Ib), having no additional sequence or one base additional sequence of A at the 5' side of the nucleotide sequence represented by formula (Ib), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of the phosphodiester bonds are replaced by phosphorothioate bonds. The total length of the oligodeoxynucleotide may be 28 to 200-nucleotide length (preferably 30 to 100-nucleotide length, more preferably 35 to 80-nucleotide length, further preferably 40 to 65-nucleotide length, still further preferably 43 to 57-nucleotide length).

A nucleotide sequence represented by formula (Ib) may be the nucleotide sequence represented by SEQ ID NO: 12, 55, 56, 57, 58, 59, 21, 60, 61, 62, 63, 64, 68 or 94.

In a further aspect, in one embodiment, the oligodeoxynucleotide of the present invention comprises a CpG oligodeoxynucleotide comprising a nucleotide sequence represented by formula (Ia):

$$5'X\text{-CpG-}Y_1Y_2Y_3Y_4Y_5Y_6Y_7\text{-CpG-}TZ3' \quad \text{(Ia)}$$

wherein X is T, $Y_1Y_2Y_3Y_4Y_5Y_6Y_7$ is a nucleotide sequence selected from the group consisting of TTTTTTT, TTTTTTA, TTCGTTT, TTCGTTA and AGCGAG, and Z is T, having no additional sequence or an additional sequence selected from the group consisting of C, T, CT and CTC (preferably C or T) at the 3' side of the nucleotide sequence represented by formula (Ia), having no additional sequence or one base additional sequence of A at the 5' side of the nucleotide sequence represented by formula (Ta), and consisting of 13, 14 or 15 bases, and a polydeoxyadenylic acid having 20 to 60-nucleotide length (preferably 20 to 50 nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of the phosphodiester bonds are replaced by phosphorothioate bonds. The total length of the oligodeoxynucleotide may be generally 28 to 200-nucleotide length (preferably 30 to 100-nucleotide length, more preferably 35 to 80-nucleotide length, further preferably 40 to 65-nucleotide length, still further preferably 43 to 57-nucleotide length).

A nucleotide sequence represented by formula (Ia) may be the nucleotide sequence represented by SEQ ID NO: 95, 96, 97, 98 or 99.

As the oligodeoxynucleotide of the present invention, Compound 4, 6, 7, 8, 12, 13, 14, 15, 16, 17, 18, 19, 20, 21, 22, 25, 26, 27, 28, 29, 30, 31, 36, 37, 38, 41, 42, 43, 44, 45, 46 or 47 described below can be exemplified.

The oligodeoxynucleotide of the present invention includes any pharmacologically acceptable salts, esters, and salts of such esters, of the above-described oligodeoxynucleotide.

As the preferable examples of the pharmacologically acceptable salts of the oligodeoxynucleotide of the present invention, metal salts including alkali metal salts such as sodium salt, potassium salt and lithium salt, alkali earth metal salts such as calcium salt and magnesium salt, aluminum salt, ferric salt, zinc salt, copper salt, nickel salt, cobalt salt or the like; amine salts including inorganic salts such as ammonium salt, organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzyl ethylenediamine salt, chloroprocaine salt, procaine salt, diethanolamine salt, N-benzyl-phenethylamine salt, piperazine salt, tetramethylammonium salt, tris(hydroxymethyl) aminomethane salt or the like; inorganic acid salts including hydrohalogenide such as hydrofluoride, hydrochloride, hydrobromide and hydroiodide, nitrate, perchlorate, sulfate, phosphate or the like; organic acid salts including lower alkane sulfonates such as methanesulfonate, trifluoromethanesulfonate and ethanesulfonate, arylsulfonates such as benzenesulfonate and p-toluenesulfonate, acetate, malate, fumarate, succinate, citrate, tartrate, oxalate, maleate or the like; and amino acid salts such as glycine salt, lysine salt, arginine salt, ornithine salt, glutamate and aspartate can be mentioned.

While the oligodeoxynucleotide of the present invention may take any form of single strand, double strand and triple strand, it is preferably single strand.

The oligodeoxynucleotide of the present invention is preferably isolated. The term "isolated" means that an operation to remove factors other than the object component has been performed, and the component is not in the state of natural presence. The purity of the "isolated oligodeoxynucleotide" (percentage of the weight of the intended oligodeoxynucleotide in the total weight of the evaluation object) is generally 70% or more, preferably 80% or more, more preferably 90% or more, further preferably 99% or more.

Since the oligodeoxynucleotide of the present invention forms a complex having triple helix structure with two chains of β-1,3-glucan (e.g., schizophyllan) to exhibit a superior immunostimulatory activity, it is useful for preparing the complex of the present invention or the pharmaceutical composition of the present invention described below.

2. Complex

The present invention provides a complex containing the above-described oligodeoxynucleotide of the present invention and a β-1,3-glucan (hereinafter to be referred to as the complex of the present invention).

The CpG ODN contained in the above-described oligodeoxynucleotide of the present invention is poor in an immunostimulatory activity (e.g., an activity to activate plasmacytoid dendritic cells to produce IFN-α) unique to Class A CpG ODN when used alone. However, by forming a complex with a β-1,3-glucan (e.g, schizophyllan), it obtains the immunostimulatory activity (e.g., an activity to activate plasmacytoid dendritic cells to produce IFN-α) unique to Class A CpG ODN, without requiring the sequence of Class A CpG ODN.

Examples of the β-1,3-glucan used in the present invention include schizophyllan, lentinan, scleroglucan, curdlan, pachyman, grifolan, laminaran or the like. The β-1,3-glucan is preferably those containing many 1,6-glucopyranoside branches (33 to 40% side chain rate) such as schizophyllan, lentinan and scleroglucan, and more preferably schizophyllan. A linear-structural β-1,3-glucan having no 1,6-glucopyranoside branch, such as curdlan, is also preferable.

Schizophyllan (SPG) is a known soluble β-glucan and can be isolated from *Schizophyllum commune*. SPG consists of a β-(1→3)-D-glucan main chain, and one β-(1→6)-D-glucosyl side chain per three glucoses (Tabata, K., Ito, W., Kojima, T., Kawabata, S. and Misaki A., Carbohydr. Res., 1981, 89, 1, p. 121-135). Lentinan (LNT) is a known β-1,3-1,6-glucan and can be isolated from shiitake mushroom. The molecule formula of lentinan is $(C_6H_{10}O_5)n$ and the representative molecular weight is about 300,000 to 700,000.

As used herein, the term "complex" means a product obtained by association of multiple molecules via a noncovalent bond, such as electrostatic bond, van der Waals bond, hydrogen bond, hydrophobic interaction or the like, or a covalent bond.

The complex of the present invention preferably exhibits a triple helix structure state. In a preferred embodiment, among three chains forming the triple helix structure, two are β-1,3-glucan chains and one is a chain of the polydeoxyadenylic acid in the oligodeoxynucleotide of the present invention described above. The complex may comprise a moiety which does not contribute to the formation of the triple helix structure in part.

The composition ratio of the oligodeoxynucleotide and the β-1,3-glucan in the complex of the present invention may vary according to the length of the polydeoxyadenylic acid chain in the oligodeoxynucleotide, the length of the β-1,3-glucan or the like. For example, when the length of the β-1,3-glucan chain is equivalent to that of the polydeoxyadenylic acid chain, two chains of β-1,3-glucan and one chain of the oligodeoxynucleotide of the present invention may associate each other to form the triple helix structure. Generally, the length of the polydeoxyadenylic acid chain is shorter than the β-1,3-glucan chain, a multiple number of oligodeoxynucleotides of the present invention may associate with two chains of β-1,3-glucan to form the triple helix structure.

The complex of the present invention contains the oligodeoxynucleotide of the present invention described above and a β-1,3-glucan (e.g., schizophyllan, curdlan), and preferably consists of the oligodeoxynucleotide of the present invention and a β-1,3-glucan (e.g., schizophyllan, curdlan).

In one embodiment, the complex of the present invention contains an oligodeoxynucleotide and a β-1,3-glucan (e.g., schizophyllan, curdlan), wherein the oligodeoxynucleotide comprises a CpG oligodeoxynucleotide comprising a nucleotide sequence represented by formula (Ib):

$$5'X\text{-CpG-}Y_1Y_2\text{—CpG-TZ}3' \qquad \text{(Ib)}$$

wherein X is T, $Y_1$ is a base selected from the group consisting of A, G and T, $Y_2$ is not present or is a base selected from the group consisting of A, G and T, and Z is T, having no additional sequence or an additional sequence of 1 to 3 bases (i.e., 1, 2 or 3 bases) at the 3' side of the nucleotide sequence represented by formula (Ib), having no additional sequence at the 5' side of the nucleotide sequence represented by formula (Ib), and consisting of 8 to 16 bases (preferably 8 to 12 bases), and a polydeoxyadenylic acid having 20 to 60-nucleotide length (preferably 30 to 50-nucleotide length, more preferably 30 to 45-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end of the polydeoxyadenylic acid, some or all of the phosphodiester bonds are replaced by phosphorothioate bonds, and the total length is 28 to 200-nucleotide length (preferably 30 to 100-nucleotide length, more preferably 35 to 80-nucleotide length, further preferably 40 to 65-nucleotide length, still further preferably 43 to 57-nucleotide length).

In one embodiment the complex of the present invention comprises an oligodeoxynucleotide and a β-1,3-glucan (e.g., schizophyllan, curdlan), wherein the oligodeoxynucleotide comprises a CpG oligodeoxynucleotide comprising a nucleotide sequence represented by a formula (Ib):

$$5'X\text{-CpG-}Y_1Y_2\text{-CpG-TZ}3' \quad \text{(Ib)}$$

wherein

X is T, $Y_1Y_2$ is AG, AA, AT, TA, TT, GA, A, T, C or G (preferably, AG, AA, AT, TA, TT, GA, A, T or G), and Z is T, having no additional sequence or an additional sequence selected from the group consisting of C, CT and CTC at the 3' side of the nucleotide sequence represented by formula (Ib), having no additional sequence at the 5' side of the nucleotide sequence represented by formula (Ib), and consisting of 8 to 16 bases (preferably 8 to 12 bases), and a polydeoxyadenylic acid having 20 to 60-nucleotide length (preferably 30 to 50-nucleotide length, more preferably 30 to 45-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end of the polydeoxyadenylic acid, some or all of the phosphodiester bonds are replaced by phosphorothioate bonds, and the total length is 28 to 200-nucleotide length (preferably 30 to 100-nucleotide length, more preferably 35 to 80-nucleotide length, further preferably 40 to 65-nucleotide length, and still further preferably 43 to 57-nucleotide length).

The nucleotide sequence represented by formula (Ib) may be the nucleotide sequence represented by SEQ ID NO: 12, 55, 56, 57, 58, 59, 21, 60, 61, 62, 63 or 64.

In a further aspect, in one embodiment, the complex of the present invention contains an oligodeoxynucleotide and a β-1,3-glucan (e.g., schizophyllan, curdlan), wherein the oligodeoxynucleotide comprises a CpG oligodeoxynucleotide comprising a nucleotide sequence represented by formula (I):

$$5'X\text{-CpG-L-CpG-TZ}3' \quad \text{(I)}$$

wherein X is T,

L is a nucleotide sequence consisting of 1 to 7 bases, and

Z is T, having no additional sequence or an additional sequence of 1 to 3 bases (i.e., 1, 2 or 3 bases) at the 3' side of the nucleotide sequence represented by formula (I), having no additional sequence or one base additional sequence at the 5' side of the nucleotide sequence represented by formula (I), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of phosphodiester bonds are replaced by phosphorothioate bonds. The total length of the oligodeoxynucleotide may be generally 28 to 200-nucleotide length (preferably 30 to 100-nucleotide length, more preferably 35 to 80-nucleotide length, further preferably 40 to 65-nucleotide length, still further preferably 43 to 57-nucleotide length). L may be a nucleotide sequence selected from the group consisting of A, G, C, T, AA, AG, AT, GA, GT, TA, TT, TTTTTTT, TTTTTTA, TTCGTTT, TTCGTTA and AGCGAG.

In a further aspect, in one embodiment, the complex of the present invention contains an oligodeoxynucleotide and a β-1,3-glucan (e.g., schizophyllan, curdlan), wherein the oligodeoxynucleotide comprises a CpG oligodeoxynucleotide comprising a nucleotide sequence represented by a formula (Ib):

$$5'X\text{-CpG-}Y_1Y_2\text{-CpG-TZ}3' \quad \text{(Ib)}$$

wherein

X is T, $Y_1$ is a base selected from the group consisting of A, G and T, $Y_2$ is not present or is a base selected from the group consisting of A, G and T, and Z is T, having no additional sequence or an additional sequence of 1 to 3 bases (i.e., 1, 2 or 3 bases) at the 3' side of the nucleotide sequence represented by formula (Ib), having no additional sequence or one base additional sequence at the 5' side of the nucleotide sequence represented by formula (Tb), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of the phosphodiester bonds are replaced by phosphorothioate bonds. The total length of the oligodeoxynucleotide may be 28 to 200-nucleotide length (preferably 30 to 100-nucleotide length, more preferably 35 to 80-nucleotide length, further preferably 40 to 65-nucleotide length, still further preferably 43 to 57-nucleotide length).

In a further aspect, in one embodiment, the complex of the present invention contains an oligodeoxynucleotide and a β-1,3-glucan (e.g., schizophyllan, curdlan), wherein the oligodeoxynucleotide comprises a CpG oligodeoxynucleotide comprising a nucleotide sequence represented by formula (Ib):

$$5'X\text{-CpG-}Y_1Y_2\text{-CpG-TZ}3' \quad \text{(Ib)}$$

wherein X is T, $Y_1Y_2$ is AG, AA, AT, TA, TT, GA, GT, A, T, C or G (preferably, AG, AA, AT, TA, TT, GA, GT, A, T or G), and Z is T, having no additional sequence or an additional sequence selected from the group consisting of C, T, CT and CTC at the 3' side of the nucleotide sequence represented by formula (Ib), having no additional sequence or one base additional sequence of A at the 5' side of the nucleotide sequence represented by formula (Ib), and consisting of 8 to 16 bases (preferably 8 to 15 bases, more preferably 8 to 12 bases), and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, some or all of the phosphodiester bonds are replaced by phosphorothioate bonds. The total length of the oligodeoxynucleotide may be 28 to 200-nucleotide length (preferably 30 to 100-nucleotide length, more preferably 35 to 80-nucleotide length, further preferably 40 to 65-nucleotide length, still further preferably 43 to 57-nucleotide length). The nucleotide sequence represented by formula (Ib) may be the nucleotide sequence represented by SEQ ID NO: 12, 55, 56, 57, 58, 59, 21, 60, 61, 62, 63, 64, 68 or 94.

In a further aspect, in one embodiment, the complex of the present invention contains an oligodeoxynucleotide and a β-1,3-glucan (e.g., schizophyllan, curdlan), wherein the oligodeoxynucleotide comprises a CpG oligodeoxynucleotide comprising a nucleotide sequence represented by formula (Ia):

$$5'X\text{-}CpG\text{-}Y_1Y_2Y_3Y_4Y_5Y_6Y_7\text{-}CpG\text{-}TZ3' \quad \text{(Ia)}$$

wherein X is T, $Y_1Y_2Y_3Y_4Y_5Y_6Y_7$ is a nucleotide sequence selected from the group consisting of TTTTTTT, TTTTTTA, TTCGTTT, TTCGTTA and AGCGAG, and Z is T, having no additional sequence or an additional sequence selected from the group consisting of C, T, CT and CTC (preferably C or T) at the 3' side of the nucleotide sequence represented by formula (Ia), having no additional sequence or one base additional sequence of A at the 5' side of the nucleotide sequence represented by formula (Ia), and consisting of 13, 14 or 15 bases, and a polydeoxyadenylic acid having 20 to 60-nucleotide length (preferably 20 to 50-nucleotide length, more preferably 20 to 40-nucleotide length, further preferably 25 to 40-nucleotide length);

wherein the polydeoxyadenylic acid is linked to the 3' side of the CpG oligodeoxynucleotide via no spacer sequence, the CpG oligodeoxynucleotide is located at the most 5' end, the polydeoxyadenylic acid is located at the most 3' end, or an additional sequence is linked to the 3' end side of the polydeoxyadenylic acid, and some or all of the phosphodiester bonds are replaced by phosphorothioate bonds. The total length of the oligodeoxynucleotide may be generally 28 to 200-nucleotide length (preferably 30 to 100-nucleotide length, more preferably 35 to 80-nucleotide length, further preferably 40 to 65-nucleotide length, still further preferably 43 to 57-nucleotide length).

The nucleotide sequence represented by formula (Ia) may be the nucleotide sequence represented by SEQ ID NO: 95, 96, 97, 98 or 99.

In one embodiment, the complex of the present invention contains an oligodeoxynucleotide and a β-1,3-glucan (e.g., schizophyllan, curdlan), wherein the oligodeoxynucleotide is a compound selected from the group consisting of the Compounds 4, 6, 7, 8, 12, 13, 14, 15, 16, 17, 18, 19, 20, 21, 22, 25, 26, 27, 28, 29, 30, 31, 36, 37, 38, 41, 42, 43, 44, 45, 46 and 47 described below.

The complex of the present invention can be prepared according to the methods described in JP2018-100616A; WO2015/04131; Sakurai et al., Biomacromolecules 2, 641-650 (2001); Shimada et al., Bioconjugate chemistry 18, 1280-1286 (2007); Koyama et al., Science translational medicine 2, 25ra24 (2010); Minari et al., Bioconjugate chemistry 22, 9-15 (2011) or the like. That is, the β-1,3-glucan which is present as a triple helix structure in nature is dissolved in an aprotic organic polar solvent (dimethyl sulfoxide (DMSO), acetonitrile, acetone or the like) or an aqueous alkaline solution (sodium hydroxide, potassium hydroxide, ammonia, calcium hydroxide or the like) to be loosened into single strands. A solution of the thus-obtained single strand β-1,3-glucan and a solution (an aqueous solution, a buffered aqueous solution at near neutral pH, or an acidic buffered aqueous solution, preferably, an aqueous solution or a buffered aqueous solution at near neutral pH) of the oligodeoxynucleotide of the present invention are mixed, the pH is adjusted to a near neutral pH as necessary, and the mixture is maintained for a suitable time, for example, overnight at 5° C. As a result, two β-1,3-glucan chains and one poly(dA) chain in the oligodeoxynuelcotide of the present invention form a triple helix structure, thereby forming the complex of the present invention. Oligodeoxynucleotides which have not formed the complex can be removed by subjecting the generated complex to purification by size-exclusion chromatography, ultrafiltration, dialysis or the like. In addition, the β-1,3-glucan which have not formed the complex can be removed by subjecting the generated complex to purification by anion exchange chromatography. The complex can be appropriately purified by the above-mentioned methods.

Formation of the complex of the present invention can be confirmed by measuring, for example, conformational changes by CD (circular dichroism) spectroscopy, UV absorption shift by size-exclusion chromatography, gel electrophoresis, microchip electrophoresis, capillary electrophoresis, though the method is not limited thereto.

While of the mixing ratio of the oligodeoxynucleotide of the present invention and the β-1,3-glucan can be appropriately set in consideration of the length of the poly(dA) chain or the like, the molar ratio (β-1,3-glucan/ODN) is usually 0.005 to 10.0.

The complex of the present invention is preferably isolated. The purity of the "isolated complex" (the percentage of the weight of the complex of interest in the total weight of the evaluation object) is usually 70% or more, preferably 80% or more, more preferably 90% or more, and further preferably 99% or more.

Since the complex of the present invention has a superior immunostimulatory activity and high activity to induce IFN-α production (e.g., activity to activate plasmacytoid dendritic cells (preferably human plasmacytoid dendritic cells) to produce IFN-α), it is useful as an immunostimulating agent or the like.

3. Pharmaceutical Composition

The present invention provides a pharmaceutical composition comprising the oligodeoxynucleotide of the present invention and a β-1,3-glucan (e.g., schizophyllan, curdlan) described above. In a preferred embodiment, the oligodeoxynucleotide of the present invention forms a complex with the β-1,3-glucan (e.g., schizophyllan, curdlan) (i.e., the complex of the present invention). That is, the pharmaceutical composition of the present invention preferably comprises the complex of the present invention described above. The pharmaceutical composition of the present invention can be obtained by formulating the above-mentioned oligodeoxynucleotide of the present invention and a β-1,3-glucan (e.g., schizophyllan, curdlan), or the complex of the present invention described above according to a conventional means. The pharmaceutical composition of the present invention may contain a pharmacologically acceptable carrier in addition to the oligodeoxynucleotide of the present invention and the β-1,3-glucan (e.g., schizophyllan, curdlan), or the complex of the present invention described above. The pharmaceutical composition may further contain an antigen (detailed below). Such pharmaceutical composition is provided in a dosage form suitable for oral or parenteral administration.

As a composition for parenteral administration, for example, injection, suppository or the like may be used, and the injection may include dosage forms such as intravenous injection, subcutaneous injection, intradermal injection, muscular injection, drip injection and the like. Such injections can be prepared according to a known method. The preparation method of the injection includes dissolving or suspending a combination of the oligodeoxynucleotide of the present invention and a β-1,3-glucan (e.g., schizophyllan, curdlan), or the complex of the present invention described above in a sterile aqueous solvent generally used for injection. As the aqueous solvent for injection, for example, distilled water; physiological saline; buffers such as phosphate buffer, carbonate buffer, tris buffer, acetate buffer or the like can be used. The pH of such aqueous solvent is, for example, 5 to 10, preferably 6 to 8. Prepared injection is preferably filled in a suitable ampoule.

A powder preparation comprising a combination of the oligodeoxynucleotide of the present invention and a β-1,3-glucan (e.g., schizophyllan, curdlan) or the complex of the present invention may also be prepared by subjecting a solution or a suspension comprising the combination of the oligodeoxynucleotide of the present invention and a β-1,3-glucan (e.g., schizophyllan, curdlan) or the complex of the present invention to vacuum drying, freeze-drying, or other treatment. The combination of the oligodeoxynucleotide of the present invention and a β-1,3-glucan (e.g., schizophyllan, curdlan) or the complex of the present invention can be provided for use by storing same in a powder form and dissolving or dispersing the powder in an aqueous solvent for injection at the time of use.

When the pharmaceutical composition of the present invention comprises the combination of the oligodeoxynucleotide and a β-1,3-glucan (e.g., schizophyllan, curdlan), the molar ratio of the oligodeoxynucleotide and the β-1,3-glucan (e.g., schizophyllan, curdlan) (β-1,3-glucan/ODN) is not particularly limited, but is, for example, 0.005 to 10.0.

The content of the combination of the oligodeoxynucleotide of the present invention and a β-1,3-glucan (e.g., schizophyllan, curdlan) or the complex of the present invention in the pharmaceutical composition is, for example, about 0.1 to 100 wt %, preferably about 1 to 99 wt %, more preferably about 10 to 90 wt % of the whole pharmaceutical composition.

The pharmaceutical composition of the present invention may contain the combination of the oligodeoxynucleotide of the present invention and a β-1,3-glucan (e.g., schizophyllan, curdlan) or the complex of the present invention as active ingredients alone or in combination with other active ingredients.

4. Medical Use

Since the complex of the present invention has a superior immunostimulatory activity, the complex and the pharmaceutical composition of the present invention can be used as an immunostimulating agent. By administrating the complex or the pharmaceutical composition of the present invention to a mammal (primates such as human, rodents such as mouse or the like), an immune response can be induced in the mammal. Particularly, since the complex of the present invention stimulates peripheral blood mononuclear cells and strongly induces type I interferon (Pan-IFN-α, IFN-α2 or the like) production, it is useful as a type I interferon production-inducing agent. Since the production of type I interferon is induced, the complex of the present invention and the pharmaceutical composition containing same are useful for the prophylaxis or treatment of a disease for which type I interferon is effective. Examples of the disease for which type I interferon is effective include virus infection (e.g., hepatitis C virus (HCV), herpes virus, papilloma virus, RS virus, influenza virus or the like), cancer or the like.

Also, the complex of the present invention has a strong vaccine adjuvant activity, and by administrating the complex of the present invention together with an antigen to a mammal a strong immune response to the antigen can be induced. Accordingly, the present invention also provides a composition for inducing an immune response to an antigen, which contains (a) the complex of the present invention, and (b) the antigen. The complex of the present invention strongly augments a humoral immune response (antigen-specific antibody production) or a cellular immune response (antigen-specific CTL induction) to the antigen. Therefore, the complex and the pharmaceutical composition of the present invention, particularly the complex of the present invention and the pharmaceutical composition containing same are useful as a vaccine adjuvant. As used herein, the adjuvant refers to a pharmaceutic aid that promotes an immune response, which is a substance that non-specifically enhances an immune response to an antigen when administered with the antigen to the living body.

The antigen is not particularly limited as long as it is antigenic to a mammal (primates such as human, rodents such as mouse or the like) being the subject of administration, and can be recognized as an antigen by an antibody or a cytotoxic T lymphocyte (CTL, $CD8^+$ T cell), Any substance which can be an antigen (proteins, peptides, nucleic acids, lipids, carbohydrates, and modifications of these substances (e.g., modifications in which deletion, substitution, and/or addition or the like of one or more amino acids (hereinafter mutations etc.) are introduced) can be used. As the antigen, for example, an antigen derived from a pathogen such as protozoa, fungi, bacterium, virus or the like, and an antigen relating a particular disease such as cancer or the like can be used, but are not limited to.

As used herein, the term "antigen A is derived from pathogen X" means that antigen A is contained in said pathogen X as a constituent factor. For example, when antigen A is a polypeptide, it means that the amino acid sequence of the polypeptide is present in the amino acid sequences of the proteins encoded in the genome of pathogen X.

Examples of the antigen derived from a pathogen include the pathogen itself or a portion thereof, an inactivated or attenuated pathogen itself or a portion thereof, or a modification thereof in which a mutation or the like is introduced, or the like.

When an antigen derived from a pathogen is used as the antigen, an immune response to the antigen is induced, and a mechanism for immunologically eliminating the pathogen containing the antigen from the body is constructed. Therefore, a composition comprising (a) the complex of the present invention, and (b) an antigen derived from a pathogen, for inducing an immune response to the antigen, is useful for the prophylaxis or treatment of an infection of the pathogen.

The complex of the present invention strongly induces a humoral immune response (antigen-specific antibody production) or a cellular immune response (antigen-specific CTL induction) to the antigen. Particularly, the complex of the present invention strongly induces type I interferon. Type I interferons play an important role in innate immune responses or activating an acquired immunity after virus infection. Type I interferon induces expression of co-stimulatory molecules including CD40, CD80, CD86 or the like and MHC molecules, matures dendritic cells (DC) and promotes the cross-presentation of viral antigens. Type I interferons also induce chemokines to migrate lymphocytes and monocytes to the inflammation site. In addition, type I interferons are involved in the activation and growth of the cytotoxic T cells ($CD8^+$ T cells), and maintenance of memory $CD8^+$ T cells, Therefore, antigens derived from intracellular infectious pathogens (virus, protozoa, fungi, bacterium or the like) known to be recognized by cytotoxic T lymphocytes, an antigen related to a cancerous cell (e.g., tumor antigen) or the like are preferably used as the antigen.

Examples of the intracellular infectious virus include, but are not particularly limited to, RS virus, influenza virus, parainfluenza virus, hepatitis C virus (HCV), hepatitis A virus (HAV), hepatitis B virus (HBV), ebolavirus, cytomegalovirus, adenovirus, poliovirus, Japanese encephalitis virus, measles virus, mumps virus, rubella virus, rabies virus, yellow fever virus, varicella zoster virus, hantavirus, dengue virus, norovirus, rotavirus, parvovirus, corona virus, distemper virus, adult T cell leukemia virus (HTLV-1), human immunodeficiency virus (HIV), herpes virus, papillomavirus or the like. Examples of the intracellular infectious bacteria include mycoplasma or the like. Examples of the intracellular infectious protozoa include malaria plasmodium, schistosome or the like. The intracellular infectious pathogen is preferably a virus (specifically, RS virus, influenza virus or the like).

Examples of the antigen associated with cancerous cells include proteins, sugar chains, and peptides that are specifically expressed in the cancerous cells, as well as variants (deletions, substitutions, and/or additions) of the aforementioned substances, modifications thereof or the like.

For example, by administering a composition comprising (a) the complex of the present invention, and (b) an antigen derived from a pathogen or cancer, for inducing an immune response to said antigen to a patient with the infection of said pathogen or cancer or to a mammal (e.g., human) having a risk to be affected with the infection of said pathogen or cancer, an activity of the cytotoxic T lymphocytes (CTLs) is enhanced, and production of antibodies specific to said antigen is induced or enhanced in the subject who received the administration, i.e., a protective immune response is induced or enhanced in the mammal (e.g., human), whereby said infection and cancer can be prevented or treated. Accordingly, the composition is useful for the prophylaxis or treatment of the diseases such as above-described infection, cancer or the like.

A composition for inducing an immune response to an antigen comprising (a) the complex of the present invention, and (b) said antigen can be prepared in a manner similar to the pharmaceutical composition of the present invention described above.

All references cited in the present specification, including publication, patent document and the like, are hereby incorporated individually and specifically by reference, to the extent that the entireties thereof have been specifically disclosed herein.

The present invention is explained in more detail in the following by referring to Examples, which are not to be construed as limitative.

EXAMPLES

Example 1

The CpG ODNs listed in Table 6 below were synthesized by Ajinomoto Bio-Pharma Services, GeneDesign Inc. and KNC Laboratories Co. These oligodeoxynucleotides were synthesized using the conventional solid-phase phosphoramidite method. (M. H. Caruthers. A brief review of DNA and RNA chemical synthesis. Biochem. Soc. Trans., 2011, 39, 575-580.)

TABLE 6

| SEQ ID NO: | | | |
|---|---|---|---|
| CpG ODN | Total length | Sequence (5'→3') CpG ODNs-dA(s)40 | Compound Name |
| 1 | 28 | TsCsGsTsCsGsAsAsAsAsAsAsAsAsAsAsAsAsAsAsAsAsAsAsAs<br>AsAsAsAsAsAsAsAsAsAsAsAsAsAsAsAsAsAsAsAsA | 1 |
| 2 | 29 | AsTsCsGsTsCsGsAsAsAsAsAsAsAsAsAsAsAsAsAsAsAsAsAsAs<br>AsAsAsAsAsAsAsAsAsAsAsAsAsAsAsAsAsAsAsAsAsAsA | 2 |
| 3 | 30 | GsAsTsCsGsTsCsGsAsAsAsAsAsAsAsAsAsAsAsAsAsAsAsAsAs<br>AsAsAsAsAsAsAsAsAsAsAsAsAsAsAsAsAsAsAsAsAsAsAsA | 3 |
| 4 | 31 | TsCsGsTsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsAsA | 4 |
| 5 | 32 | GsTsCsGsTsTsAsAsAsAsAsAsAsAsAsAsAsAsAsAsAsAsAsAsAs<br>AsAsAsAsAsAsAsAsAsAsAsAsAsAsAsAsAsAsAsAsA | 5 |
| 6 | 33 | TsCsGsAsGsCsGsTsTsCsTsCsAsAsAsAsAsAsAsAsAsAsAsAsAsAs<br>AsAsAsAsAsAsAsAsAsAsAsAsAsAsAsAsAsAsAsAsAsAsAsAsAsA | 6 |

TABLE 6-continued

| SEQ ID NO: CpG ODN | SEQ ID NO: Total length | Sequence (5'→3') CpG ODNs-dA(s)40 | Compound Name |
|---|---|---|---|
| 7 | 34 | TsCsGsTsTsCsGsTsTsCsTsCsAsAsAsAsAsAsAsAsAsAsAsAsAsAsA<br>sAsAsAsAsAsAsAsAsAsAsAsAsAsAsAsAsAsAsAsAsAsAsAsAsA | 7 |
| 8 | 35 | TsCsGsAsGsCsGsTsTsCsAsAsAsAsAsAsAsAsAsAsAsAsAsAsAs<br>AsAsAsAsAsAsAsAsAsAsAsAsAsAsAsAeAsAsAsAsAsAsAsAsA | 8 |
| 9 | 36 | TsCsGsAsGsCsGsTsAsAsAsAsAsAsAsAsAsAsAsAsAsAsAsAsAs<br>AsAsAsAsAsAsAsAsAsAsAsAsAsAsAsAsAsAsAsAsAsAsA | 9 |
| 10 | 37 | AsGsCsGsTsTsAsAsAsAsAsAsAsAsAsAsAsAsAsAsAsAsAsAsAs<br>AsAsAsAsAsAsAsAsAsAsAsAsAsAsAsAsAsAsAsAsA | 10 |
| 11 | 38 | AsTsCsGsAsCsAsAsAsAsAsAsAsAsAsAsAsAsAsAsAsAsAsAsAs<br>AsAsAsAsAsAsAsAsAsAsAsAsAsAsAsAsAsAsAsAsA | 11 |
| 12 | 39 | TsCsGsAsGsCsGsTsTsAsAsAsAsAsAsAsAsAsAsAsAsAsAsAsAs<br>AsAsAsAsAsAsAsAsAsAsAsAsAsAsAsAsAsAsAsAsAsAsAsA | 12 |
| 13 | 40 | TsCsGsAsGsCsGsTsTsCsTsAsAsAsAsAsAsAsAsAsAsAsAsAsAsAs<br>AsAsAsAsAsAsAsAsAsAsAsAsAsAsAsAsAsAsAsAsAsAsAsAsA | 13 |
| 14 | 41 | AsCsTsCsTsCsGsAsGsCsGsTsTsCsTsCsAsAsAsAsAsAsAsAsAsAsAsAsAs<br>AsAsAsAsAsAsAsAsAsAsAsAsAsAsAsAsAsAsAsAsAsAsAsAsAsAsA | 14 |
| 15 | 42 | TsCsGsAsAsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 15 |
| 16 | 43 | TsCsGsGsAsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 16 |
| 17 | 44 | TsCsGsTsAsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 17 |
| 18 | 45 | TsCsGsAsTsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 18 |
| 19 | 46 | TsCsGsAsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsA | 19 |
| 20 | 47 | TsCsGsGsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsA | 20 |
| 21 | 48 | TsCsGsAsCsGsTsTsAsAsAsAsAsAsAsAsAsAsAsAsAsAsAsAsAs<br>AsAsAsAsAsAsAsAsAsAsAsAsAsAsAsAsAsAsAsAsAsAsA | 21 |
| 22 | 49 | TsCsGsAsCsGsTsTsTsAsAsAsAsAsAsAsAsAsAsAsAsAsAsAsAs<br>AsAsAsAsAsAsAsAsAsAsAsAsAsAsAsAsAsAsAsAsAsAsAsA | 22 |
| 23 | 50 | TsGsTsAsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsA | 23 |
| 24 | 51 | TsCsTsAsCsGsTsTsAsAsAsAsAsAsAsAsAsAsAsAsAsAsAsAsAs<br>AsAsAsAsAsAsAsAsAsAsAsAsAsAsAsAsAsAsAsAsAsAsA | 24 |
| 25 | 52 | TsCsGsCsCsGsTsCsTsAsAsAsAsAsAsAsAsAsAsAsAsAsAsAsAs<br>AsAsAsAsAsAsAsAsAsAsAsAsAsAsAsAsAsAsAsAsAsAsAsA | 25 |
| 26 | 53 | TsCsGsCsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsA | 26 |
| 27 | 54 | CsCsGsAsCsGsTsTsCsAsAsAsAsAsAsAsAsAsAsAsAsAsAsAsAs<br>AsAsAsAsAsAsAsAsAsAsAsAsAsAsAsAsAsAsAsAsAsAsAsA | 27 |

The s in the above sequence indicates a phosphorothioate bond between the nucleosides, Details are described for Compounds 6, 8, 9, 10 and 18 from the above list. Table 7 shows the molecular weights of the CpG ODN-dA40s of the sequences described above and retention times analyzed using a reversed-phase HPLC. (Analysis condition column: Waters, X-Bridge C18 2.5 μm, 4.6×100 nm, solution A: 8 mM triethylamine, 100 mM hexafluoroisopropanol, solution B: methanol, solution B gradient: 5%→30% (20 min), temperature: 60° C., flow rate: 1 mL/min, wavelength: 260 nm)

TABLE 7

| Compound Name | Calculated Value | Measured Value | Retention Time (min) |
|---|---|---|---|
| 6 | 16947.8 | 16946.9 | 18.1 |
| 8 | 16322.7 | 16321.5 | 18.0 |
| 9 | 15697.7 | 15696.7 | 17.9 |
| 10 | 15047.6 | 15047.0 | 17.9 |
| 18 | 16297.7 | 16297.8 | 18.2 |

[Experimental Example 1] Formation of the Complex of CpG ODN-dA(s)40 and SPG (Schizophyllan)

0.25 mol/L sodium hydroxide solution was added to adjust the concentration of the SPG solution to 15 mg/mL and stirred until the solid was completely dissolved. To the 110 μM nucleic acid aqueous solution, a volume of 0.3 M sodium dihydrogen phosphate aqueous solution equal to the SPG solution was added and stirred. The SPG solution was added to the resulting nucleic acid solution and stirred overnight. The mixing ratio of the solution was 0.27 mole of SPG to 1 mole of the nucleic acid. Complex formation was confirmed by monitoring the absorption at 260 nm for a shift of the CpG ODN signal toward the high molecular weight side by using a size exclusion chromatography (System: ACQUITY UPLC H-Class system (Waters), Pre-column: Asahipak GF-1G 7B (Shodex), Column: Asahipak GF7M-HIQ (Shodex) two columns were connected, Flow rate: 0.6 mL/min, Buffer: 10 mM EDTA PBS, temperature 40° C.). Only complexes that exhibited a complexation rate of 90% or higher were used. In the evaluation of the activity of CpG ODN-dA(s)40s in the following Experimental Examples, the complexes of said CpG ODN-dA(s)40s and SPG were used in all experiments.

[Experimental Example 2] Comparative Evaluation of the Activity of K3, Compound 6 and Compound 7

CpG ODN-dA (s)40/SPG complex was added to human PBMCs (Frozen NPB-MNC: AllCells, PB003F lot. 3018992) and the cells were incubated for 24 hours ($1.0\times10^5$ cells/100 μL/well x 96 well plate, duplicate). The IFN alpha concentration in the supernatant was measured by ELISA (Human IFN alpha (pan specific) ELISA development kit 3425-1H-6 (Mabtech AB)).

Class B CpG is a phosphorothioate-backbone CpG ODN of 12 or more bases, and those having longer base length are known to have higher immune activity (Verthelyi, D., Ishii, K. J., Gursel, M. & Klinman, D. M. Human Peripheral Blood Cells Differentially Recognize and Respond to Two Distinct CpG Motifs. J. Immunol. 2001, 166, 2372-2377). It has been reported that when K3, a Class B CpG, is complexed with SPG, it has both the immunostimulatory activity of Class B CpG (stimulating B cells to produce IL-6) and that of Class A CpG (acting on pDCs to produce IFN alpha) (WO2015/041318). To investigate the effect of shortening the base length of the CpG ODN, the present inventors have evaluated the ability of Compound 6/SPG complex and Compound 7/SPG complex, in which the CpG moiety is 12-base long, and K3-dA(s)40/SPG complex to induce IFN alpha production.

As shown in FIG. 1, both the Compound 6/SPG and Compound 7/SPG complexes showed higher IFN alpha production-inducing ability than the K3-dA(s)40/SPG complex, where K3 is 20-base long while the CpG ODN moiety of Compound 6 and Compound 7 is 12-base long. These results suggest that the complex with a shorter CpG ODN moiety has a higher IFN alpha production-inducing ability.

[Experimental Example 3] Evaluation of the Activity of Short Chain CpG ODN-dA(s)40/SPG Complexes Using Human PBMCs TLR9 has two binding sites for ODN and (1) 5'-$X_1CX_2$-3' and (2) CpG motif bind to each corresponding site (Umehara Ohto. Immunity 2018, 48, 1-10). Since the present inventors assumed that the IFN alpha producing capacity would be increased by minimizing the number of bases while having these two binding sequences, these two binding sequences were evaluated in the present invention.

CpG ODN-dA(s)40/SPG complex was added to human PBMCs (CTL, Cat.CTL-UP1, Sample ID #HHU20190711), and the cells were incubated for 24 hours ($5.0 \times 10^5$ cells/100 μL/well x 96 well plate, duplicate). The IFN alpha concentration in the supernatant was measured by Bio-Plex (BIO-RAD: Bio-Plex pro Reagent kitIII #171304090M, humans cytokine Screening Panel Standard #12007919, IFN alpha2 Set #171B6010M).

Figure 2:
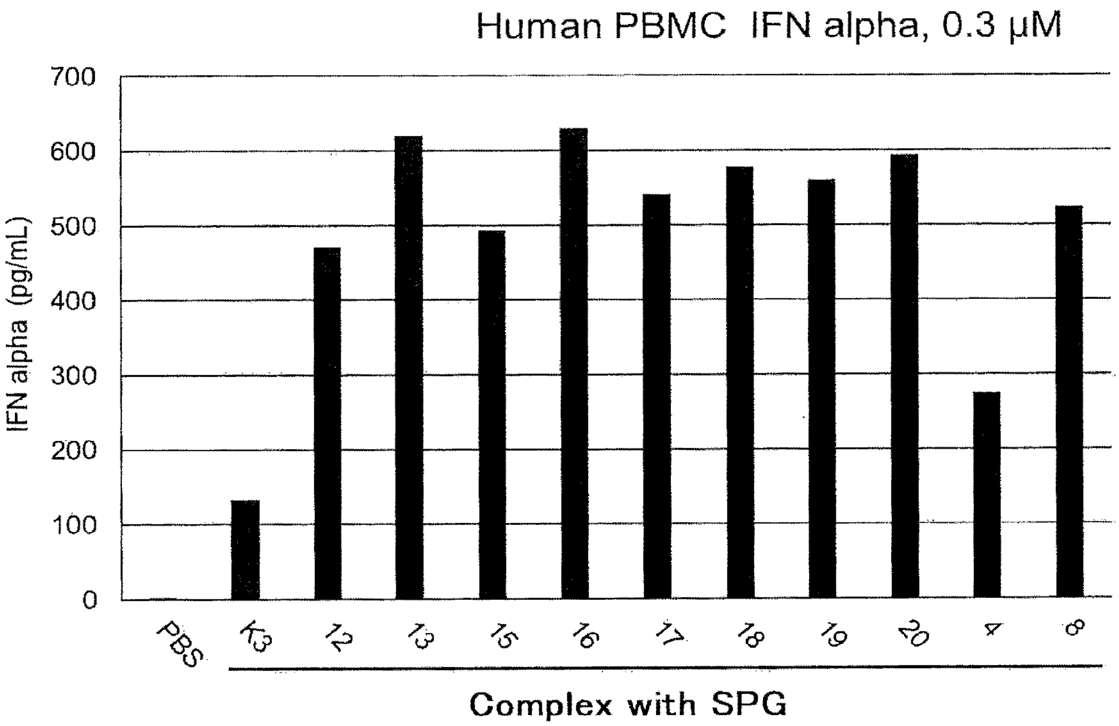
FIG. 2 shows the activity of the complex of CpG ODN-dA40 and schizophyllan to induce human PBMC IFN-α production. The numbers on the horizontal axis indicate the name of compounds.
Figure 3:
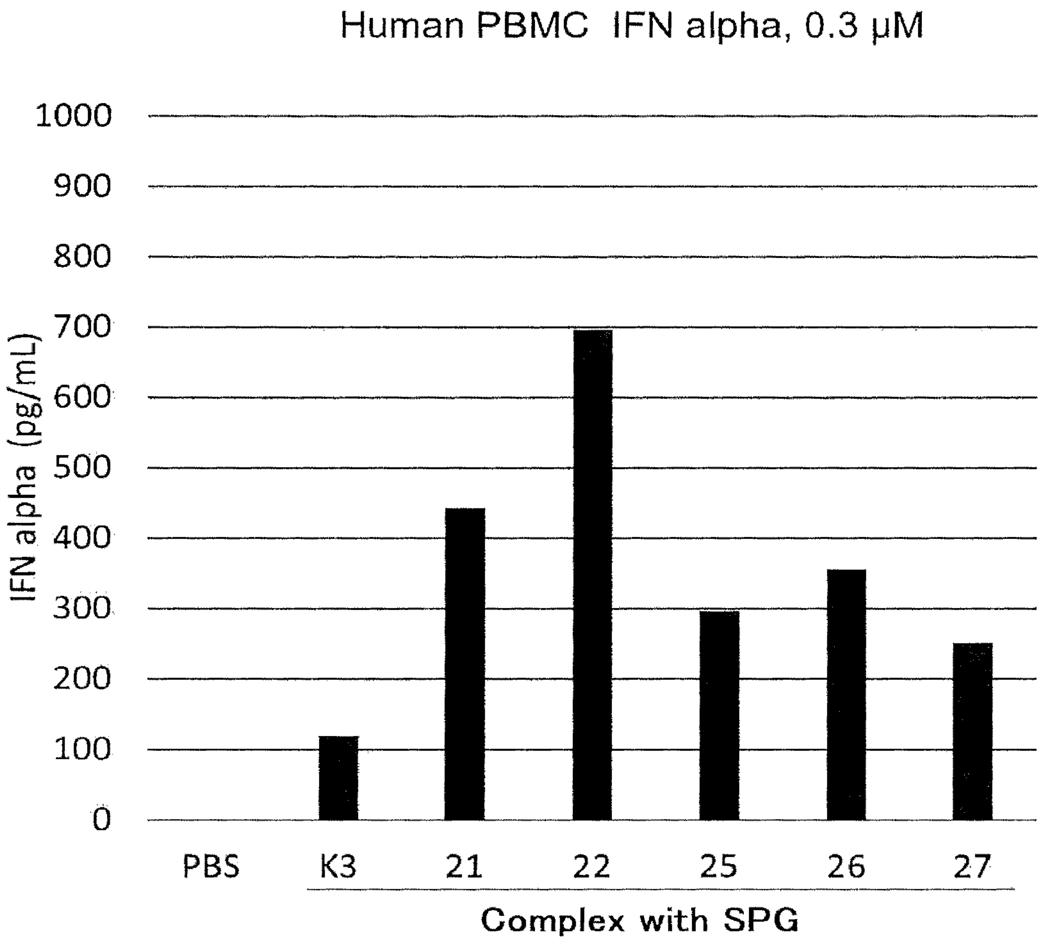
FIG. 3 shows the activity of the complex of CpG ODN-dA40 and schizophyllan to induce human PBMC IFN-α production. The numbers on the horizontal axis indicate the name of compounds.

The results are shown in FIGS. 2 and 3. It was found that CpG ODNs, which are shorter than the base length considered necessary in CpG ODNs such as K3 (12 bases or more) (Non-Patent Document 2), exhibit high immunostimulatory effect (IFN alpha production-inducing effect) when complexed with SPG.

The complexes including Compound 1/SPG, Compound 2/SPG, Compound 3/SPG, Compound 5/SPG, Compound 9/SPG, Compound 10/SPG, Compound 11/SPG, Compound 23/SPG and Compound 24/SPG had very low or little IFN alpha production-inducing activity.

[Experimental Example 4] Evaluation of the Activity Using Mouse Splenocytes

CpG ODN-dA(s)40/SPG complex was added to mouse (C57BL/6J, female, 8 weeks) splenocytes and the cells were incubated for 24 hours ($1.0\times10^6$ cells/100 μL/well, 96 well plate, duplicate). The IFN alpha in the supernatant was measured by ELISA (IFN alpha Mouse ELISA Kit Thermo Fisher Scientific #BMS6027).

Figure 4:
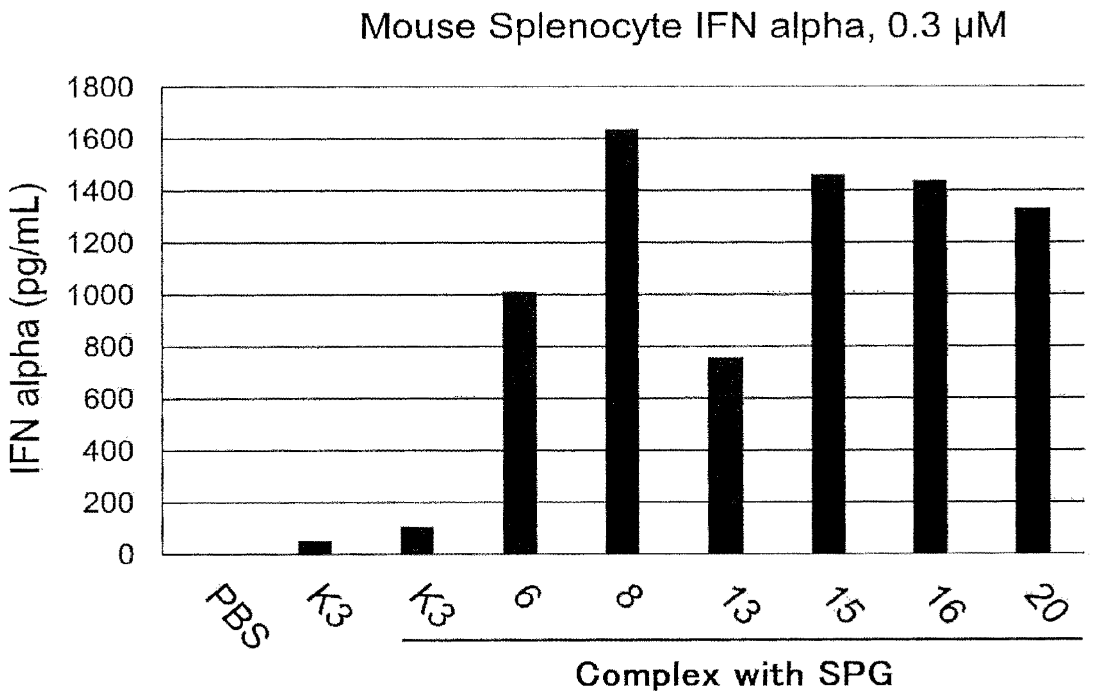
FIG. 4 shows the activity of the complex of CpG ODN-dA40 and schizophyllan to induce mouse splenocyte IFN-α production. The numbers on the horizontal axis indicate the name of compounds.

The results are shown in FIG. 4. Similar to human PBMCs, the complex of the present invention induced IFN alpha production in mouse splenocytes more potently than the existing K3-dA(s)40/SPG complex.

[Experimental Example 5] Evaluation of In Vivo Activity in Mice

CpG ODN-dA(s)40/SPG complex was injected into the tail vein of mice (C57BL/6J, female, 8 weeks, n=3) (1.5 nmol/200 μL/head). 6 hours later, blood was collected and IFN alpha concentration in plasma was determined by ELISA (IFN alpha Mouse ELISA Kit Thermo Fisher Scientific #BMS6027).

Figure 5:
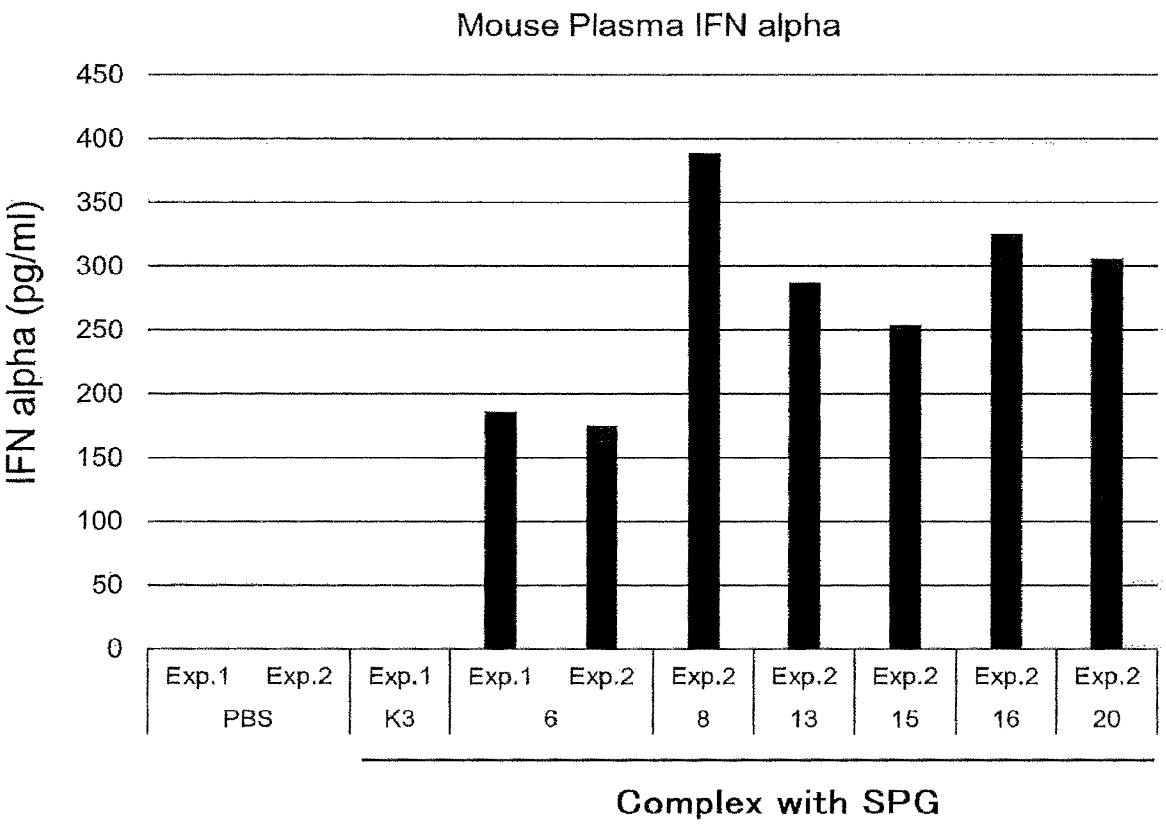
FIG. 5 shows the activity of the complex of CpG ODN-dA40 and schizophyllan to induce IFN-α production in vivo. The numbers on the horizontal axis indicate the name of compounds.

The results are shown in FIG. 5. K3-dA(s)40/SPG complex showed little induction of IFN alpha production. On the other hand, the CpG ODN-dA(s)40/SPG complex of the present invention showed high IFN alpha production-inducing ability in mice in vivo. To date, no case has been reported in which CpG was administered into mice tail vein and increase in IFN alpha in plasma was observed. The results suggest that the complex of the present invention have a superior immunostimulatory effect.

Example 2

The CpG ODNs listed in Table 8 below were synthesized by Ajinomoto Bio-Pharma Services, GeneDesign Inc. and KNC Laboratories Co. Ltd. These oligodeoxynucleotides were synthesized by using the conventional solid-phase phosphoramidite method. (M. H. Caruthers. A brief review of DNA and RNA chemical synthesis. Biochem. Soc. Trans., 2011, 39, 575-580.)

TABLE 82

| SEQ ID NO: | | | |
|---|---|---|---|
| CpG ODN | Total length | Sequence (5'→3') CpG ODNs-dA(s)n (n: 20-40) | Compound Name |
| 20 | 78 | TsCsGsGsCsGsTsTsCsAsAsAsAsAsAsAsAsAsAsAsAsAsAsAsAs<br>AsAsAsAsAsAsAsAsAsAsAsAsAsAsAsAsAsAsA | 28 |
| 20 | 79 | TsCsGsGsCsGsTsTsCsAsAsAsAsAsAsAsAsAsAsAsAsAsAsAsAs<br>AsAsAsAsAsAsAsAsAsAsAsAsAsA | 29 |
| 20 | 80 | TsCsGsGsCsGsTsTsCsAsAsAsAsAsAsAsAsAsAsAsAsAsAsAsAs<br>AsAsAsAsAsAsAsAsA | 30 |
| 20 | 81 | TsCsGsGsCsGsTsTsCsAsAsAsAsAsAsAsAsAsAsAsAsAsAsAsAs<br>AsAsAsA | 31 |
| 20 | 47 | TsCsGGCsGTTCsAsAsAsAsAsAsAsAsAsAsAsAsAsAsAsAsAsAs<br>AsAsAsAsAsAsAsAsAsAsAsAsAsAsAsAsAsAsAsAsAsA | 32 |
| 20 | 47 | TsCGsGCGsTTCsAsAsAsAsAsAsAsAsAsAsAsAsAsAsAsAsAsAs<br>AsAsAsAsAsAsAsAsAsAsAsAsAsAsAsAsAsAsAsAsAsA | 33 |
| 20 | 47 | TsCGGCGTTCsAsAsAsAsAsAsAsAsAsAsAsAsAsAsAsAsAsAsA<br>sAsAsAsAsAsAsAsAsAsAsAsAsAsAsAsAsAsAsAsAsA | 34 |
| 20 | 47 | TCGGCGTTCsAsAsAsAsAsAsAsAsAsAsAsAsAsAsAsAsAsAsAs<br>AsAsAsAsAsAsAsAsAsAsAsAsAsAsAsAsAsAsAsAsA | 35 |
| 66 | 82 | AsTsCsGsGsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 36 |
| 67 | 83 | TsCsGsGsTsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 37 |
| 68 | 84 | TsCsGsAsCsGsTsCsAsAsAsAsAsAsAsAsAsAsAsAsAsAsAsAsAs<br>AsAsAsAsAsAsAsAsAsAsAsAsAsAsAsAsAsAsAsAsAsAsA | 38 |
| 69 | 85 | TsCsGsAsCsGsAsTsCsAsAsAsAsAsAsAsAsAsAsAsAsAsAsAsAs<br>AsAsAsAsAsAsAsAsAsAsAsAsAsAsAsAsAsAsAsAsAsAsAsA | 39 |
| 70 | 86 | TsCsGsAsCsGsCsCsCsAsAsAsAsAsAsAsAsAsAsAsAsAsAsAsAs<br>AsAsAsAsAsAsAsAsAsAsAsAsAsAsAsAsAsAsAsAsAsAsAsA | 40 |
| 71 | 87 | GsAsTsCsGsTsCsGsTsTsCsAsAsAsAsAsAsAsAsAsAsAsAsAsAs<br>AsAsAsAsAsAsAsAsAsAsAsAsAsAsAsAsAsAsAsAsAsAsAsAsAs<br>A | 41 |
| 72 | 88 | AsTsCsGsTsCsGsTsTsCsAsAsAsAsAsAsAsAsAsAsAsAsAsAsAs<br>AsAsAsAsAsAsAsAsAsAsAsAsAsAsAsAsAsAsAsAsAsAsAsAsA | 42 |
| 73 | 89 | TsCsGsTsTsTsTsTsTsTsCsGsTsTsTsAsAsAsAsAsAsAsAsAsAsA<br>sAsAsAsAsAsAsAsAsAsAsAsAsAsAsAsAsAsAsAsAsAsAsAsAsA<br>sAsAsAsA | 43 |
| 74 | 90 | TsCsGsTsTsTsTsTsTsAsCsGsTsTsCsAsAsAsAsAsAsAsAsAsAsA<br>sAsAsAsAsAsAsAsAsAsAsAsAsAsAsAsAsAsAsAsAsAsAsAsAsA<br>sAsAsAsA | 44 |
| 75 | 91 | TsCsGsTsTsCsGsTsTsTsCsGsTsTsTsAsAsAsAsAsAsAsAsAsAsA<br>sAsAsAsAsAsAsAsAsAsAsAsAsAsAsAsAsAsAsAsAsAsAsAsAsA<br>sAsAsAsA | 45 |

TABLE 82-continued

| SEQ ID NO: CpG ODN | SEQ ID NO: Total length | Sequence (5'→3') CpG ODNs-dA(s)n (n: 20-40) | Compound Name |
|---|---|---|---|
| 76 | 92 | TsCsGsTsTsCsGsTsTsAsCsGsTsTsCsAsAsAsAsAsAsAsAsAsAsAsAsAsAsAsAsAsAsAsAsAsAsAsAsAsAsAsAsAsAsAsAsAsAsAsAsAsAsAsA | 46 |
| 77 | 93 | TsCsGsAsGsCsGsAsGsCsGsTsTsCsAsAsAsAsAsAsAsAsAsAsAsAsAsAsAsAsAsAsAsAsAsAsAsAsAsAsAsAsAsAsAsAsAsAsAsAsAsAsA | 47 |

The s in the above sequence indicates a phosphorothioate bond between the nucleosides.

Compounds 28, 29, 30, and 31 have the same CpG ODN (TsCsGsGsCsGsTsTsC) (SEQ TD NO: 20) as Compound 21, but the length of the poly dA(s) is different from Compound 21. The length of poly dA(s) in Compound 21 is 40, while those in Compounds 28, 29, 30 and 31 are 35, 30, 25 and 20, respectively. Compounds 32, 33, 34, and 35 have the same CpG ODN sequence (SEQ ID NO: 20) and the same length of poly dA(s) (dA(s) 40) as Compound 21, but the number and position of phosphorothioate bonds in the CpG ODN differ from Compound 21.

Details are described for Compounds 28, 29 and 30 from the above list. The molecular weights and the retention times of Compounds 28, 29 and 30, analyzed using a reversed-phase HPLC, are shown.
(Analysis condition column: Waters, X-Bridge C18 2.5 μm, 4.6x75 nm, solution A: 8 mM triethylamine, 100 mM hexafluoroisopropanol, solution B: methanol, solution B gradient: 5%-+30% (20 min), temperature: 60° C., flow rate: 1 mL/min, wavelength: 260 nm)

TABLE 9

| Compound Name | Calculated Value | Measured Value | Retention Time (min) |
|---|---|---|---|
| 28 | 14359.2 | 14362.7 | 12.8 |
| 29 | 12712.8 | 12711.5 | 12.9 |
| 30 | 11066.4 | 11065.3 | 12.7 |

[Experimental Example 6] Evaluation of In Vivo Activity in Mice

CpG ODN-dA (s)n/SPG complex was injected into the tail vein of mice (C57BL/6J, female, 8 weeks) (0.5 nmol/200 μL/head). 6 hours later, blood was collected and IFN alpha concentration in plasma was determined by ELISA (IFN alpha Mouse ELISA Kit Thermo Fisher Scientific #BMS6027).

Figure 6:
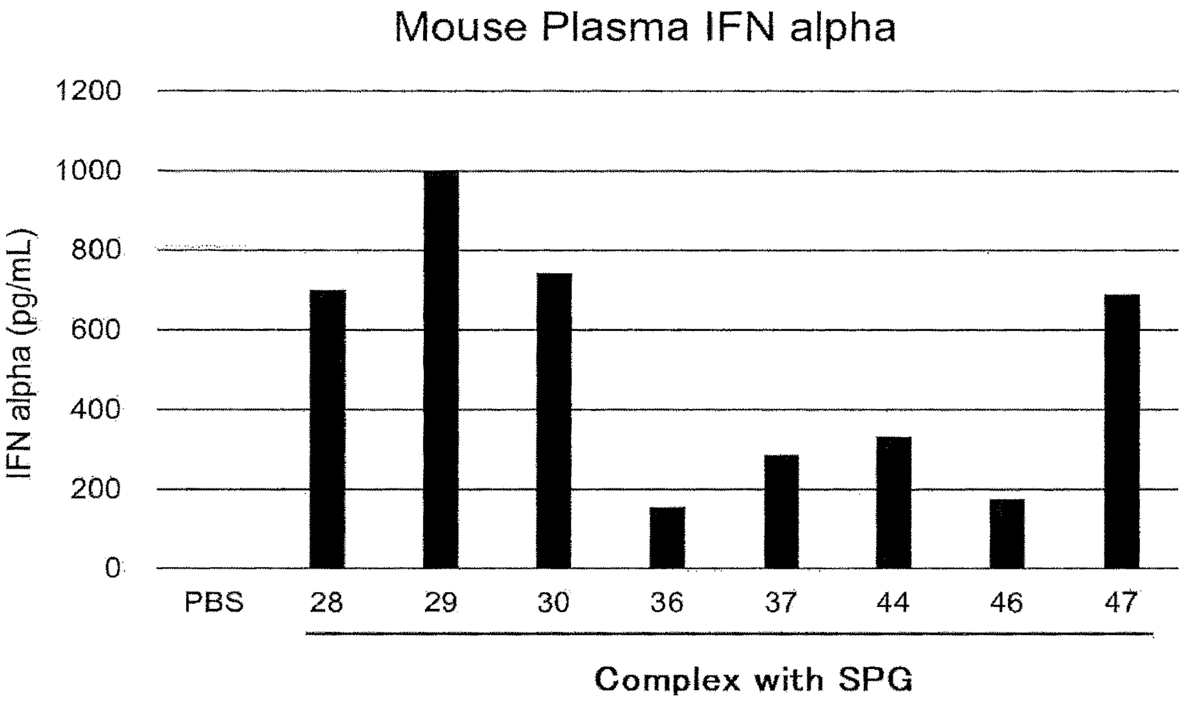
FIG. 6 shows the activity of the complex of CpG ODN-dA40 and schizophyllan to induce IFN-α production in vivo. The numbers on the horizontal axis indicate the name of compounds.

The results are shown in FIG. 6. The CpG ODN-dA (s)n/SPG complex of the present invention showed high IFN alpha production-inducing ability in mice in vivo. The results for Compounds 28, 29, and 30 suggest that the IFN alpha production-inducing ability of the complex is maintained even when the length of the poly dA(s) is less than 40.

[Experimental Example 7] Evaluation of In Vivo Activity in Mice

CpG ODN-dA (s)n/SPG complex was injected into the tail vein of mice (C57BL/6J, female, 8 weeks) (0.5 nmol/200 μL/head). 6 hours later, blood was collected and IFN alpha concentration in plasma was determined by ELISA (IFN alpha Mouse ELISA Kit Thermo Fisher Scientific #BMS6027).

Figure 7:
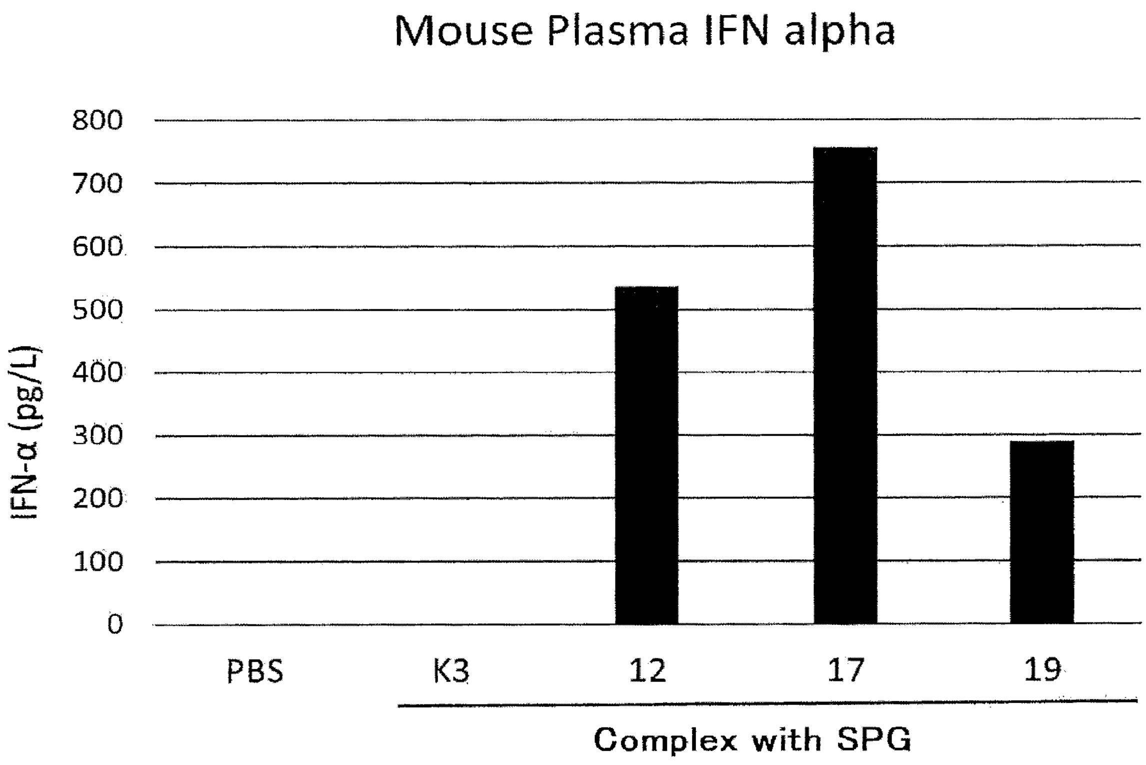
FIG. 7 shows the activity of the complex of CpG ODN-dA40 and schizophyllan to induce IFN-α production in vivo. The numbers on the horizontal axis indicate the name of compounds.

The results are shown in FIG. 7. The CpG ODN-dA (s)n/SPG complex of the present invention showed high IFN alpha production-inducing ability in mice in vivo.

[Experimental Example 8] Evaluation of the Activity of CpG ODN-dA (s)n/Curdlan Complex The complex of Compound 20 and Curdlan was formed according to Experimental Example 1, except that Curdlan was used instead of SPG. Compound 20/Curdlan complex was added to human PBMCs (CTL, Cat. CTL-UP1, Sample HHU20190709) and the cells were incubated for 24 hours ($5.0\times10^5$ cells/100 μL/well x 96 well plate, duplicate). The IFN alpha concentration in the supernatant was measured by ELISA IFN alpha Human Matched Antibody Pair, Thermo Fisher Scientific, #BMS216MST).

Figure 8:
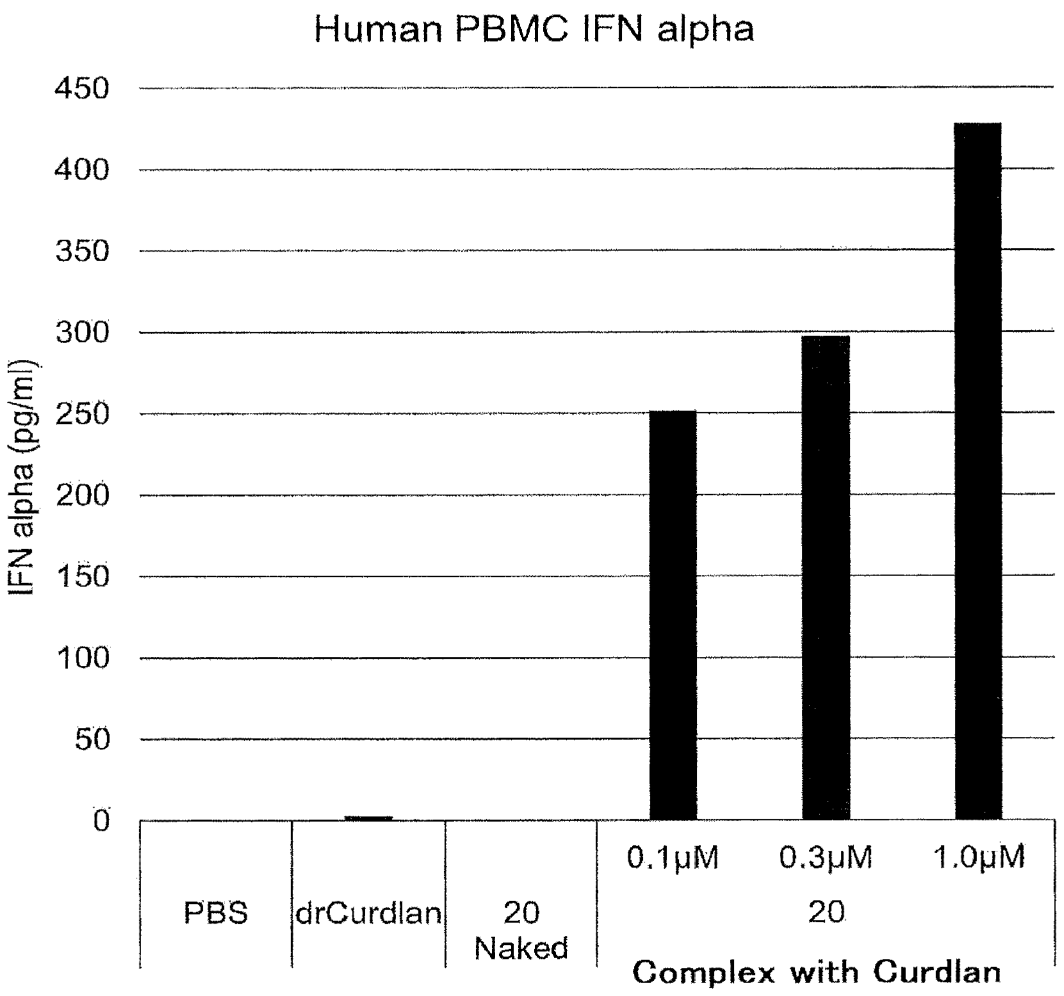
FIG. 8 shows the activity of the complex of CpG ODN-dA40 and curdlan to induce human PBMC IFN-α production. The numbers on the horizontal axis indicate the name of compounds.

The results are shown in FIG. 8. "Naked" in the figure indicates Compound 20 that has not formed a complex with Curdlan. In addition, "drCurdlan" is a Curdlan that has been subjected to the denaturation and regeneration treatment as in the preparation of the Compound 20/Curdlan complex. The concentration of drCurdlan is equivalent to the concentration of Curdlan in the 1000 nM CpG ODN-dA(s)40/Curdlan complex. Compound 20/Curdlan complex induced IFN alpha production in human PBMCs in a same manner as Compound 20/SPG complex. These results suggest that the immunostimulatory activity of the complex is maintained even when Curdlan is used as a β-glucan.

[Experimental Example 9] Evaluation of the Activity of Short Chain CpG ODN-dA (s)40/SPG Complex Using Human PBMCs CpG ODN-dA (s)n/SPG complex was added to human PBMCs (CTL, Cat. CTL-UP1, Sample HHU20200611) and the cells were incubated for 24 hours ($5.0\times10^5$ cells/100 μL/well x 96 well plate, duplicate). The IFN alpha concentration in the supernatant was measured by ELISA (IFN alpha Human Matched Antibody Pair, Thermo Fisher Scientific, #BMS216MST).

Figure 9:
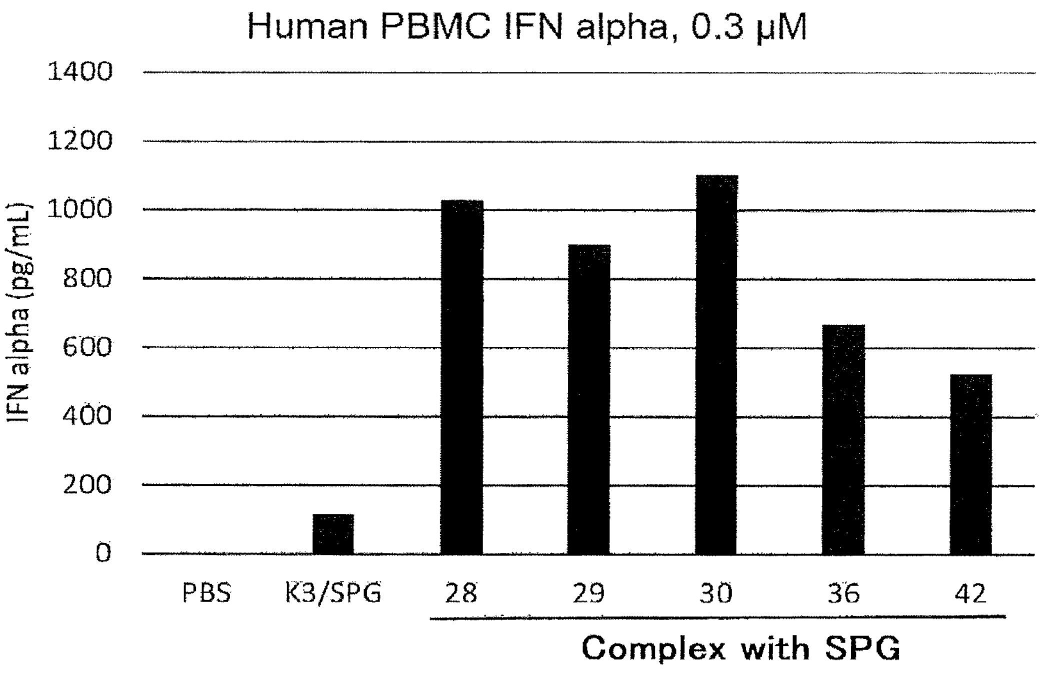
FIG. 9 shows the activity of the complex of CpG ODN-dA40 and schizophyllan to induce human PBMC IFN-α production. The numbers on the horizontal axis indicate the name of compounds.

The results are shown in FIG. 9. The CpG ODN-dA(s)n of the present invention showed high immunostimulatory effect (IFN alpha production-inducing effect) when complexed with SPG. Since Compound 36/SPG complex and Compound 42/SPG complex have significant immunostimulatory effect, it was suggested that the immunostimulatory activity of the complexes is maintained even when an additional sequence of at least one base is linked to the 5' side of the nucleotide sequence of formula (I). On the other hand, the complexes including Compound 39/SPG and Compound 40/SPG had very low or almost no IFN alpha production-inducing activity.

[Experimental Example 10] Evaluation of the Activity of Short Chain CpG ODN-dA (s)40/SPG Complex Using Human PBMCs CpG ODN-dA (s)40/SPG complex was added to human PBMCs (CTL, Cat. CTL-UP1, Sample #HHU20190709) and the cells were incubated for 24 hours ($5.0\times10^5$ cells/100 μL/well x 96 well plate, duplicate). The IFN alpha concentration in the supernatant was measured by ELISA (IFN alpha Human Matched Antibody Pair, Thermo Fisher Scientific, #BMS216MST). Compounds 43, 44, 45, 46 and 47 were used as CpG ODN-dA (s)40. These compounds are characterized in that the nucleotide length between the two CpGs is 6 or 7 bases and the base length of the CpG ODN moiety is 14 or 15.

Figure 10:
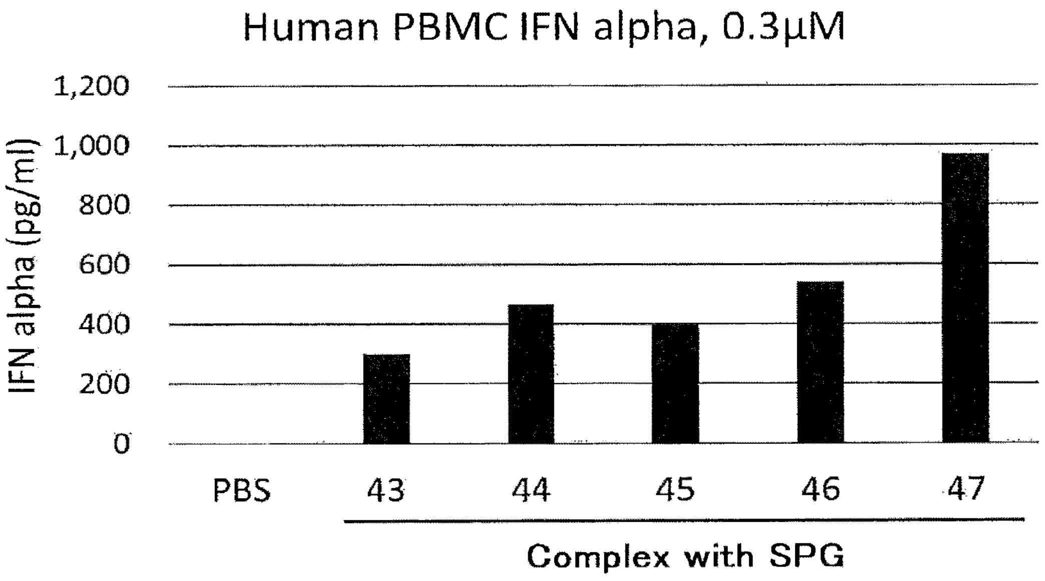
FIG. 10 shows the activity of the complex of CpG ODN-dA40 and schizophyllan to induce human PBMC IFN-α production. The numbers on the horizontal axis indicate the name of compounds.

The results are shown in FIG. 10. The evaluated CpG ODN-dA(s)40s showed high immunostimulatory effect (IFN alpha production-inducing effect) when complexed with SPG. It was suggested that the immunostimulatory activity of the complex of the present invention is maintained even when the nucleotide length between the two CpGs in the CpG ODN is extended to 6 or 7 bases. It was also suggested that the immunostimulatory activity of the complex of the present invention is maintained even when the base length of the CpG ODN moiety is extended to 14 or 15 bases.

INDUSTRIAL APPLICABILITY

The present invention provides an oligodeoxynucleotide and a complex containing same having a strong type I interferon production-inducing activity. Since the complex of the present invention has a strong type I interferon production-inducing activity, it is useful as an immunostimulating agent for activating innate immunity or acquired immunity (especially cellular immunity) or a vaccine adjuvant.

This application is based on a patent application No. 2019-235078 filed in Japan (filing date: Dec. 25, 2019), the contents of which are incorporated in full herein.

The invention claimed is:

1. A complex which comprises an oligodeoxynucleotide and a β-1,3-glucan;

wherein the oligodeoxynucleotide consists of a CpG oligodeoxynucleotide comprising a nucleotide sequence represented by formula (I):

5'-X-CpG-L-CpG-TZ-3' (I), wherein X is T or C,

L is a nucleotide sequence consisting of 1 to 7 bases,

Z is T or C, wherein said CpG oligodeoxynucleotide consists of 8 to 15 bases and a polydeoxyadenylic acid having a length capable of forming a complex with a β-1,3-glucan, and wherein the polydeoxyadenylic acid is linked to the 3' side of the CpG oligodeoxynucleotide.

2. The complex according to claim 1, wherein the β-1,3-glucan is schizophyllan.

3. The complex according to claim 1, wherein the β-1,3-glucan is curdlan.

4. A pharmaceutical composition which contains the complex according to claim 1.

5. The pharmaceutical composition according to claim 4, wherein the β-1,3-glucan is schizophyllan.

6. The pharmaceutical composition according to claim 4, wherein the β-1,3-glucan is curdlan.

7. A method for enhancing immune response in a mammal, which comprises administering a pharmacologically effective dose of the complex according to claim 1 to the mammal.

8. A method for inducing production of type I interferon in a mammal, which comprises administering a pharmacologically effective dose of the complex according to claim 1 to the mammal.

9. The complex according to claim 1, wherein X is T.

10. The complex according to claim 1, wherein Z is T.

11. The complex according to claim 1, wherein L is a nucleotide sequence represented by formula (II):

5'-$Y_1Y_2Y_3Y_4Y_5Y_6Y_7$-3' (II), wherein $Y_1$ is a base selected from the group consisting of A, G, T and C, and $Y_2$, $Y_3$, $Y_4$, $Y_5$, $Y_6$ and $Y_7$ are each independently not present, or are a base selected from the group consisting of A, G, T and C.

12. The complex according to claim 11, wherein $Y_3$, $Y_4$, $Y_5$, $Y_6$ and $Y_7$ are not present in formula (II).

13. The complex according to claim 12, wherein $Y_1$ is a base selected from the group consisting of A, G and T.

14. The complex according to claim 12, wherein $Y_2$ is a base selected from the group consisting of A, G and T.

15. The complex according to claim 11, wherein $Y_1$ is A or T, $Y_2$ is C or T, $Y_3$ is C or T, $Y_4$ is C or T, $Y_5$ is A or T, $Y_6$ is G or T, and $Y_7$ is not present or is A or T.

16. The complex according to claim 1, wherein L is a nucleotide sequence selected from the group consisting of A, G, C, T, AA, AG, AT, GA, GT, TA, TT, TTTTTTT, TTTTTTA, TTCGTTT, TTCGTTA and AGCGAG.

17. The complex according to claim 1, wherein the CpG oligodeoxynucleotide has no additional sequence or has an additional sequence of 1 to 3 bases at the 3' side of the nucleotide sequence represented by formula (I).

18. The complex according to claim 17, wherein the additional sequence of 1 to 3 bases is a nucleotide sequence selected from the group consisting of C, CT and CTC.

19. The complex according to claim 1, wherein the CpG oligodeoxynucleotide has no additional sequence or has one base additional sequence at the 5' side of the nucleotide sequence represented by formula (I).

20. The complex according to claim 19, wherein the one base additional sequence is A.

21. The complex according to claim 1, wherein the CpG oligodeoxynucleotide consists of 8 to 12 bases.

22. The complex according to claim 1, wherein the nucleotide sequence represented by formula (I) consists of the nucleotide sequence represented by SEQ ID NO: 12, 55, 56, 57, 58, 59, 21, 60,61, 62, 63 or 64.

23. The complex according to claim 1, wherein the nucleotide sequence represented by formula (I) consists of the nucleotide sequence represented by SEQ ID NO: 68, 94, 95, 96, 97, 98 or 99.

24. The complex according to claim 1, wherein the CpG oligodeoxynucleotide consists of the nucleotide sequence represented by SEQ ID NO: 4, 6, 7, 8, 12, 13, 14, 15, 16, 17, 18, 19, 20, 21, 22,25, 26 or 27.

25. The complex according to claim 1, wherein the CpG oligodeoxynucleotide consists of the nucleotide sequence represented by SEQ ID NO: 66, 67, 68, 71, 72, 73, 74, 75, 76 or 77.

26. The complex according to claim 1, wherein some or all of phosphodiester bonds in the oligodeoxynucleotide are replaced by phosphorothioate bonds.

27. The complex according to claim 26, wherein all of the phosphodiester bonds in the oligodeoxynucleotide are replaced by phosphorothioate bonds.

28. The complex according to claim 1, wherein the length of the polydeoxyadenylic acid is 20 to 60 bases.

29. The complex according to claim 1, which comprises the nucleotide sequence represented by SEQ ID NO: 31, 33, 34, 35, 39,40, 41, 42, 43, 44, 45, 46, 47, 48, 49, 52, 53 or 54.

30. The complex according to claim 1, which comprises the nucleotide sequence represented by SEQ ID NO: 78, 79, 80, 81, 82,83, 84, 87, 88, 89, 90, 91, 92 or 93.

* * * * *